United States Patent
Reitblat et al.

(10) Patent No.: US 11,413,029 B2
(45) Date of Patent: Aug. 16, 2022

(54) ANTERIOR TO PSOAS INSTRUMENTATION

(71) Applicant: Stryker European Operations Holdings LLC, Kalamazoo, MI (US)

(72) Inventors: Abram Reitblat, Monroe, NY (US); Steven F. Krause, Oakland, NJ (US); Spencer Popejoy, Ringwood, NJ (US); Shawn Graham, Morristown, NJ (US); Douglas G. Pedrick, Newburgh, NY (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 253 days.

(21) Appl. No.: 16/661,601

(22) Filed: Oct. 23, 2019

(65) Prior Publication Data

US 2020/0129168 A1    Apr. 30, 2020

Related U.S. Application Data

(60) Provisional application No. 62/749,856, filed on Oct. 24, 2018.

(51) Int. Cl.
    *A61B 17/02* (2006.01)
    *A61B 17/84* (2006.01)
    *A61B 17/00* (2006.01)

(52) U.S. Cl.
    CPC ........ *A61B 17/025* (2013.01); *A61B 17/0206* (2013.01); *A61B 17/846* (2013.01);
    (Continued)

(58) Field of Classification Search
    CPC ... A61B 17/02; A61B 17/025; A61B 17/0206; A61B 17/84; A61B 17/846
    See application file for complete search history.

(56) References Cited

U.S. PATENT DOCUMENTS

| 380,745 A | 4/1888 | Chamberlin |
| 1,157,202 A | 10/1915 | Bates et al. |

(Continued)

FOREIGN PATENT DOCUMENTS

| AU | 2013205982 | 12/2013 |
| FR | 2807313 A1 | 10/2001 |

(Continued)

OTHER PUBLICATIONS

Extended European Search Report for EP19205175.3 dated Mar. 19, 2020; 4 pages.

(Continued)

*Primary Examiner* — Christopher J Beccia
(74) *Attorney, Agent, or Firm* — Lerner, David, Littenberg, Krumholz & Mentlik, LLP

(57) ABSTRACT

In one embodiment, the present disclosure relates to an instrument adapted for use in an anterior to psoas spinal access procedure. The instrument includes a body, a first arm and a second arm. A first rod extends from the first arm at an angle thereto while a second rod extends from the second arm at an angle thereto. Each of the first rod and the second rod include a length with a first portion and a second portion, the first portion having a convex surface perimeter and the second portion having a perimeter different from the first portion and being convex in part. In some embodiments, a kit includes the instrument and a blade adapted for use in conjunction with the instrument in an anterior to psoas spinal access procedure.

5 Claims, 13 Drawing Sheets

(52) U.S. Cl.
CPC ............... *A61B 2017/00477* (2013.01); *A61B 2017/0256* (2013.01)

(56) References Cited

U.S. PATENT DOCUMENTS

| | | | |
|---|---|---|---|
| 1,428,653 A | 9/1922 | Nick | |
| 1,618,261 A | 2/1927 | Arbogast | |
| 1,827,497 A | 10/1931 | Varney | |
| 3,522,799 A | 8/1970 | Gauthier | |
| 3,731,673 A | 5/1973 | Halloran | |
| 3,749,088 A | 7/1973 | Kohlmann | |
| 3,782,370 A | 1/1974 | McDonald | |
| 3,796,214 A | 3/1974 | Davis | |
| 3,807,393 A | 4/1974 | McDonald | |
| 3,965,890 A | 6/1976 | Gauthier | |
| 4,010,741 A | 3/1977 | Gauthier | |
| 4,226,228 A | 10/1980 | Shin et al. | |
| 4,337,763 A | 7/1982 | Petrassevich | |
| 4,616,635 A | 10/1986 | Caspar et al. | |
| 5,052,373 A | 10/1991 | Michelson | |
| 5,092,314 A | 3/1992 | Zeitels | |
| 5,351,679 A | 10/1994 | Mayzels et al. | |
| 5,377,667 A | 1/1995 | Patton et al. | |
| 5,520,611 A | 5/1996 | Rao et al. | |
| 5,755,661 A | 5/1998 | Schwartzman | |
| 5,776,199 A | 7/1998 | Michelson | |
| 5,916,151 A | 6/1999 | Charters | |
| 5,928,139 A | 7/1999 | Koros et al. | |
| 5,931,777 A | 8/1999 | Sava | |
| 5,941,777 A | 8/1999 | Moser et al. | |
| 5,944,658 A | 8/1999 | Koros et al. | |
| 6,074,343 A | 6/2000 | Nathanson et al. | |
| 6,143,032 A | 11/2000 | Schafer et al. | |
| 6,206,826 B1 | 3/2001 | Mathews et al. | |
| 6,296,609 B1 | 10/2001 | Brau | |
| 6,354,995 B1 | 3/2002 | Hoftman et al. | |
| 6,416,465 B2 | 7/2002 | Brau | |
| 6,466,817 B1 | 10/2002 | Kaula et al. | |
| 6,564,078 B1 | 5/2003 | Marino et al. | |
| 6,616,605 B2 | 9/2003 | Wright et al. | |
| 6,719,794 B2 | 4/2004 | Gerber et al. | |
| 6,760,616 B2 | 7/2004 | Hoey et al. | |
| 6,764,491 B2 | 7/2004 | Frey et al. | |
| 6,846,287 B2 | 1/2005 | Bonadio et al. | |
| 6,849,064 B2 | 2/2005 | Hamada | |
| 6,945,933 B2 | 9/2005 | Branch et al. | |
| 7,056,321 B2 | 6/2006 | Pagliuca et al. | |
| 7,144,368 B2 | 12/2006 | Larson et al. | |
| 7,150,714 B2 | 12/2006 | Myles | |
| 7,166,073 B2 | 1/2007 | Ritland | |
| 7,195,592 B2 | 3/2007 | Ravikumar et al. | |
| 7,207,949 B2 | 4/2007 | Miles et al. | |
| 7,223,233 B2 | 5/2007 | Branch et al. | |
| 7,235,082 B2 | 6/2007 | Bartish et al. | |
| 7,261,688 B2 | 8/2007 | Smith et al. | |
| 7,326,216 B2 | 2/2008 | Bertagnoli et al. | |
| 7,329,268 B2 | 2/2008 | Van Nguyen et al. | |
| 7,374,534 B2 | 5/2008 | Dalton | |
| 7,390,298 B2 | 6/2008 | Chu | |
| 7,407,483 B2 | 8/2008 | Perez-Cruet et al. | |
| 7,435,219 B2 | 10/2008 | Kim | |
| 7,491,168 B2 | 2/2009 | Raymond et al. | |
| 7,513,869 B2 | 4/2009 | Branch et al. | |
| 7,556,600 B2 | 7/2009 | Landry et al. | |
| 7,582,058 B1 | 9/2009 | Miles et al. | |
| 7,645,232 B2 | 1/2010 | Shluzas | |
| 7,686,492 B2 | 3/2010 | Vayser et al. | |
| 7,691,057 B2 | 4/2010 | Miles et al. | |
| 7,744,612 B2 | 6/2010 | Blain | |
| 7,758,501 B2 | 7/2010 | Frasier et al. | |
| 7,780,594 B2 | 8/2010 | Hutton | |
| 7,785,253 B1 | 8/2010 | Arambula et al. | |
| 7,811,230 B2 | 10/2010 | Hsueh et al. | |
| 7,867,277 B1 | 1/2011 | Tohmeh | |
| 7,874,982 B2 | 1/2011 | Selover et al. | |
| 7,891,801 B2 | 2/2011 | Nakajima | |
| 7,905,840 B2 | 3/2011 | Pimenta et al. | |
| 7,909,761 B2 | 3/2011 | Banchieri et al. | |
| 7,918,891 B1 | 4/2011 | Curran et al. | |
| 7,920,922 B2 | 4/2011 | Gharib et al. | |
| 7,935,053 B2 | 5/2011 | Karpowicz et al. | |
| 7,976,463 B2 | 7/2011 | Dewey et al. | |
| 7,981,029 B2 | 7/2011 | Branch et al. | |
| 7,985,179 B2 | 7/2011 | Gephart et al. | |
| 7,988,623 B2 | 8/2011 | Pagliuca et al. | |
| 8,005,535 B2 | 8/2011 | Gharib et al. | |
| 8,062,217 B2 | 11/2011 | Boucher et al. | |
| 8,105,236 B2 | 1/2012 | Malandain et al. | |
| 8,137,284 B2 | 3/2012 | Miles et al. | |
| 8,152,721 B2 | 4/2012 | Michaeli et al. | |
| 8,157,728 B2 | 4/2012 | Danna et al. | |
| 8,206,293 B2 | 6/2012 | Reglos et al. | |
| 8,317,693 B2 | 11/2012 | Grey et al. | |
| 8,348,837 B2 | 1/2013 | Wenchell | |
| 8,353,826 B2 | 1/2013 | Weiman | |
| 8,376,937 B2 | 2/2013 | Xia et al. | |
| 8,409,089 B2 | 4/2013 | Michaeli et al. | |
| 8,430,813 B2 | 4/2013 | Selover et al. | |
| 8,449,463 B2 | 5/2013 | Nunley et al. | |
| 8,454,504 B2 | 6/2013 | Michaeli et al. | |
| 8,480,704 B2 | 7/2013 | Heiges et al. | |
| 8,506,629 B2 | 8/2013 | Weiland | |
| 8,506,636 B2 | 8/2013 | Dye | |
| 8,523,767 B2 | 9/2013 | DeRidder et al. | |
| 8,548,579 B2 | 10/2013 | Gharib et al. | |
| 8,568,317 B1 | 10/2013 | Gharib et al. | |
| 8,602,984 B2 | 12/2013 | Raymond et al. | |
| 8,608,652 B2 | 12/2013 | Voegele et al. | |
| 8,636,656 B2 | 1/2014 | Nichter et al. | |
| 8,663,102 B2 | 3/2014 | Michaeli et al. | |
| 8,702,600 B2 | 4/2014 | Perrow | |
| 8,758,236 B2 | 6/2014 | Albrecht et al. | |
| 8,801,608 B2 | 8/2014 | Hardenbrook | |
| 8,808,172 B2 | 8/2014 | Manzanares | |
| 8,821,394 B2 | 9/2014 | Hawkins et al. | |
| 8,852,089 B2 * | 10/2014 | Blackwell | A61B 17/0206 600/210 |
| 8,870,760 B2 | 10/2014 | Heiges et al. | |
| 8,876,687 B2 | 11/2014 | Jones et al. | |
| 8,882,661 B2 | 11/2014 | Hutton et al. | |
| 8,894,574 B2 | 11/2014 | Ellman | |
| 8,900,137 B1 | 12/2014 | Lovell et al. | |
| 8,932,360 B2 | 1/2015 | Womble et al. | |
| 8,956,283 B2 | 2/2015 | Miles et al. | |
| 8,968,363 B2 | 3/2015 | Weiman et al. | |
| 8,986,344 B2 | 3/2015 | Sandhu | |
| 8,992,425 B2 | 3/2015 | Karpowicz et al. | |
| 8,992,558 B2 | 3/2015 | Stone et al. | |
| 9,044,280 B1 * | 6/2015 | Arambula | A61B 17/0218 |
| 9,050,146 B2 | 6/2015 | Woolley et al. | |
| 9,060,757 B2 | 6/2015 | Lawson et al. | |
| 9,066,701 B1 | 6/2015 | Finley et al. | |
| 9,125,587 B2 | 9/2015 | Hawkins et al. | |
| 9,138,137 B2 | 9/2015 | Deshmukh et al. | |
| 9,138,217 B2 | 9/2015 | Smith et al. | |
| 9,220,491 B2 | 12/2015 | Nunley et al. | |
| 9,259,144 B2 | 2/2016 | Smith et al. | |
| 9,271,709 B2 | 3/2016 | Grey et al. | |
| 9,271,711 B2 | 3/2016 | Hawkins et al. | |
| 9,289,248 B2 | 3/2016 | Seex et al. | |
| 9,339,263 B2 | 5/2016 | Fenn et al. | |
| 9,351,718 B1 | 5/2016 | Arambula et al. | |
| 9,380,932 B1 | 7/2016 | Lynn et al. | |
| 9,386,916 B2 | 7/2016 | Predick et al. | |
| 9,387,009 B2 | 7/2016 | Fatone et al. | |
| 9,408,598 B1 | 8/2016 | Fantini et al. | |
| 9,451,940 B2 | 9/2016 | Spann | |
| 9,474,624 B1 | 10/2016 | Ahn | |
| 9,480,855 B2 | 11/2016 | DiMauro et al. | |
| 9,486,133 B2 | 11/2016 | Lee et al. | |
| 9,498,200 B2 | 11/2016 | Pfabe et al. | |
| 9,554,789 B2 | 1/2017 | Overes et al. | |
| 9,572,560 B2 | 2/2017 | Mast et al. | |
| 9,610,130 B2 | 4/2017 | Vayser et al. | |

(56) References Cited

U.S. PATENT DOCUMENTS

| | | |
|---|---|---|
| 9,615,818 B2 | 4/2017 | Baudouin et al. |
| 9,636,097 B2 | 5/2017 | Bass |
| 9,642,607 B2 | 5/2017 | Bootwala |
| 9,649,101 B2 | 5/2017 | Karpowicz et al. |
| 9,655,505 B1 | 5/2017 | Gharib et al. |
| 9,693,761 B2 | 7/2017 | Fedorov et al. |
| 9,782,158 B2 | 10/2017 | Nunley et al. |
| 9,788,822 B2 | 10/2017 | Miles et al. |
| 9,795,370 B2 | 10/2017 | O'Connell et al. |
| 9,808,231 B2 | 11/2017 | Miraki et al. |
| 9,808,232 B2 | 11/2017 | Heiman et al. |
| 9,848,863 B2 | 12/2017 | Cryder et al. |
| 9,895,235 B2 | 2/2018 | Melkent et al. |
| 9,918,848 B2 | 3/2018 | Waugh et al. |
| 9,968,347 B2 | 5/2018 | Hutton et al. |
| 9,980,712 B2 | 5/2018 | Seex |
| 9,987,144 B2 | 6/2018 | Seifert et al. |
| 10,004,488 B2 | 6/2018 | Simonson |
| 10,022,245 B2 | 7/2018 | Frasier et al. |
| 10,046,149 B2 | 8/2018 | Bootwala |
| 10,085,854 B2 | 10/2018 | Spann |
| 10,172,515 B2 | 1/2019 | Lee et al. |
| 10,188,376 B2 | 1/2019 | Miraki et al. |
| 10,226,353 B2 | 3/2019 | Waugh et al. |
| 10,449,059 B2 | 10/2019 | Melkent et al. |
| 10,660,631 B1 * | 5/2020 | Boesel ............... A61B 17/0206 |
| 10,716,553 B2 | 7/2020 | Spann et al. |
| 2004/0087833 A1 | 5/2004 | Bauer et al. |
| 2005/0021040 A1 | 1/2005 | Bertagnoli |
| 2006/0224045 A1 | 10/2006 | Whipple et al. |
| 2007/0060939 A1 | 3/2007 | Lancial et al. |
| 2007/0191856 A1 | 8/2007 | Gil et al. |
| 2007/0208366 A1 | 9/2007 | Pellegrino et al. |
| 2008/0319268 A1 | 12/2008 | Michaeli et al. |
| 2008/0319432 A1 | 12/2008 | Ely et al. |
| 2009/0024158 A1 | 1/2009 | Viker |
| 2009/0036746 A1 | 2/2009 | Blackwell et al. |
| 2009/0149716 A1 | 6/2009 | Diao et al. |
| 2010/0160947 A1 | 6/2010 | Akyuz et al. |
| 2012/0010472 A1 | 1/2012 | Spann |
| 2012/0010716 A1 | 1/2012 | Spann |
| 2012/0022575 A1 | 1/2012 | Mire et al. |
| 2012/0035730 A1 | 2/2012 | Spann |
| 2012/0041272 A1 | 2/2012 | Dietze, Jr. et al. |
| 2012/0046526 A1 | 2/2012 | Boettner et al. |
| 2012/0232350 A1 | 9/2012 | Seex |
| 2012/0271120 A1 | 10/2012 | Seex |
| 2013/0103103 A1 | 4/2013 | Mire et al. |
| 2013/0317303 A1 | 11/2013 | Deshmukh et al. |
| 2014/0039264 A1 | 2/2014 | Heiman |
| 2014/0039267 A1 | 2/2014 | Seex et al. |
| 2014/0114138 A1 | 4/2014 | Fedorov et al. |
| 2014/0114139 A1 | 4/2014 | Ziolo et al. |
| 2014/0142420 A1 | 5/2014 | Jackson, III |
| 2014/0172002 A1 | 6/2014 | Predick |
| 2014/0194697 A1 | 7/2014 | Seex |
| 2014/0249584 A1 | 9/2014 | Seex |
| 2014/0275801 A1 | 9/2014 | Menchaca et al. |
| 2014/0276869 A1 | 9/2014 | Tatsumi |
| 2014/0288375 A1 | 9/2014 | Miles et al. |
| 2014/0316212 A1 | 10/2014 | Reimels |
| 2014/0357946 A1 | 12/2014 | Golden et al. |
| 2015/0018625 A1 | 1/2015 | Miraki et al. |
| 2015/0045626 A1 | 2/2015 | Reimels |
| 2015/0051448 A1 | 2/2015 | Hunt et al. |
| 2015/0088030 A1 | 3/2015 | Taylor |
| 2015/0105624 A1 | 4/2015 | Martinelli et al. |
| 2015/0112148 A1 | 4/2015 | Bouquet |
| 2015/0164496 A1 | 6/2015 | Karpowicz et al. |
| 2015/0164569 A1 | 6/2015 | Reitblat et al. |
| 2015/0230749 A1 | 8/2015 | Gharib et al. |
| 2015/0230787 A1 | 8/2015 | Friedrich et al. |
| 2015/0297247 A1 | 10/2015 | Seex |
| 2015/0342589 A1 | 12/2015 | Bootwala |
| 2015/0366548 A1 | 12/2015 | Lauchner |
| 2016/0051242 A1 | 2/2016 | Predick et al. |
| 2016/0081681 A1 | 3/2016 | Waugh et al. |
| 2016/0081818 A1 | 3/2016 | Waugh et al. |
| 2016/0106408 A1 * | 4/2016 | Ponmudi ............ A61B 17/7074 606/90 |
| 2016/0120532 A1 | 5/2016 | Donald |
| 2016/0192922 A1 | 7/2016 | Friedrich et al. |
| 2016/0235448 A1 | 8/2016 | Seex |
| 2016/0278755 A1 | 9/2016 | Stone et al. |
| 2016/0296343 A1 | 10/2016 | Bost et al. |
| 2016/0361052 A1 | 12/2016 | Reimels |
| 2017/0007228 A1 | 1/2017 | Costabile |
| 2017/0027555 A1 | 2/2017 | Paumier et al. |
| 2017/0071589 A1 | 3/2017 | Simonson |
| 2017/0150956 A1 | 6/2017 | Baudouin et al. |
| 2017/0215856 A1 | 8/2017 | Martinelli et al. |
| 2017/0340317 A1 | 11/2017 | Fatone et al. |
| 2018/0064450 A1 | 3/2018 | Jackson, III |
| 2018/0333152 A1 | 11/2018 | Heiman |
| 2018/0333272 A1 | 11/2018 | Mirda et al. |
| 2019/0021716 A1 | 1/2019 | Waugh et al. |
| 2019/0105179 A1 | 4/2019 | Spann |
| 2019/0110899 A1 | 4/2019 | Waugh et al. |
| 2019/0298328 A1 | 10/2019 | Popejoy et al. |
| 2020/0305854 A1 | 10/2020 | Spann et al. |

FOREIGN PATENT DOCUMENTS

| | | |
|---|---|---|
| WO | 2008039427 A2 | 4/2008 |
| WO | 2010121291 A1 | 10/2010 |
| WO | 2015128811 A2 | 9/2015 |
| WO | 2016130878 A1 | 8/2016 |
| WO | 2017051416 A1 | 3/2017 |
| WO | 2017175024 A2 | 10/2017 |
| WO | 2018039228 A1 | 3/2018 |
| WO | 2019036048 A2 | 2/2019 |

OTHER PUBLICATIONS

Gragnaniello et al., "Anterior to psoas (ATP) fusion of the lumbar spine: evolution of a technique facilitated by changes in equipment", Journal of Spine Surgery, vol. 2, No. 4, Dec. 2016, pp. 256-265.

* cited by examiner

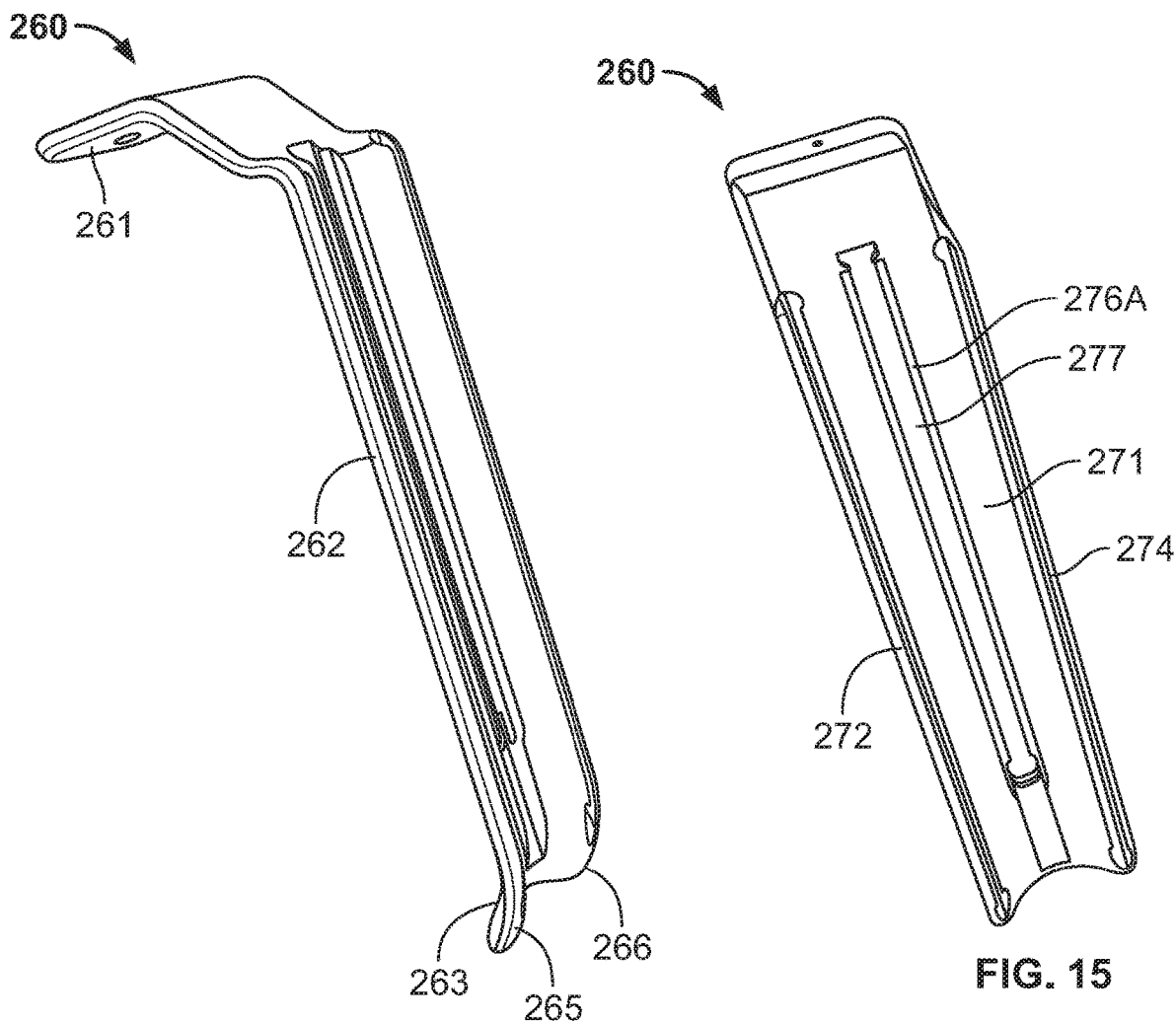
FIG. 14
FIG. 15
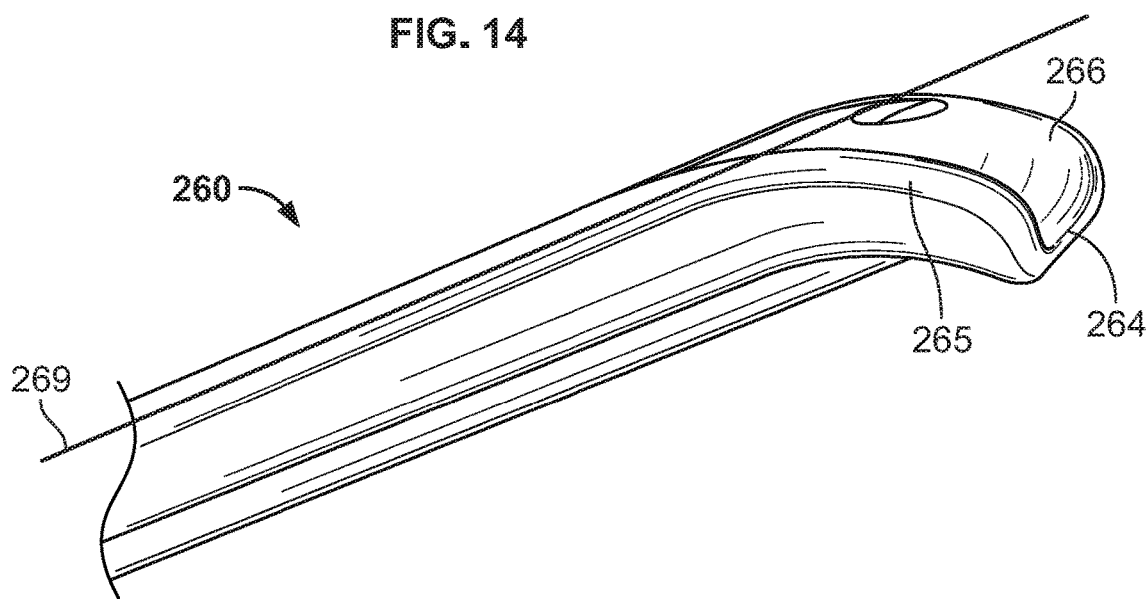
FIG. 16

ANTERIOR TO PSOAS INSTRUMENTATION

CROSS REFERENCE TO RELATED APPLICATION

This application claims the benefit of the filing date of U.S. Provisional Patent Application No. 62/749,856, filed Oct. 24, 2018, the disclosure of which is hereby incorporated by reference herein in its entirety.

BACKGROUND OF THE INVENTION

In the field of spinal surgery, an ongoing concern involves the adequacy of techniques to access surgical sites, such as different intervertebral spaces. Adequacy may be determined based on how quickly and safely a technique may be performed and whether it may be performed in a minimally invasive manner, among other considerations. Various approaches are contemplated for this purpose, including a lateral approach that requires the psoas muscle to be resected. More recently, an anterior to psoas approach has stood out as being advantageous for a number of reasons. These include, for example, the ability to access the spine without the need to perform neuromonitoring and improved access to locations on an inferior end of the spine, including the L4-L5 space for disc preparation or cage insertion. Indeed, using an anterior to psoas approach even allows access to the spine at L5-S1, a location typically unreachable with a lateral trans-psoas approach. Access to these locations is made possible in part because the anterior to psoas approach is not obstructed by the iliac crest of a patient.

However, existing anterior to psoas techniques have drawbacks, including limitations on the ability of a surgeon to hold blades and other retractor instruments in position within the body of the patient once a surgical access portal is created and on the ability to adjust the shape and size of the access portal in a controlled manner. Moreover, retractor blades having solid, arcuate surfaces may function to retract tissue, but may also limit the manner in which additional instruments for the surgical procedure may be inserted into the portal by a surgeon because such blade structures block a large portion of the surgical portal perimeter.

Thus, there is a need for improved tools and surgical techniques to perform anterior to psoas spinal surgery.

BRIEF SUMMARY OF THE INVENTION

In one aspect, the present disclosure relates to an instrument including a body, two arms and two rods. In one embodiment, the first arm has a first end adjacent to the body and a second end with a first rod attached thereto. Similarly, the second arm has a first end adjacent to the body and a second end with a second rod attached thereto. The first rod is at an angle relative to the first arm and the second rod is at an angle relative to the second arm. Additionally, at least a portion of each rod includes a convex surface perimeter.

In some embodiments, the instrument may include a pin holder having an engagement feature sized to engage with the first or second rod and may include a bone pin disposed therein. In a variant, the bone pin may protrude from each end of the pin holder. In some variants, the engagement feature of the pin holder may be a c-shaped channel.

In some embodiments, the body of the instrument may include a rack extending perpendicular to the first and second arms and one of the first and second arms may extend from a sleeve element enclosing a portion of the rack. The sleeve element may engage the rack so that it is adjustable relative to the rack in predetermined increments.

In some embodiments, each of the first and second arms may be pivotable about an axis through the body. In some variants, the body may include two handles connected at a pivot point on the axis. Each handle may be connected to a respective arm of the instrument such that movement of the handles with respect to each other causes a corresponding movement between the arms. In some embodiments, the first rod may be removable from the first arm and the second rod may be removable from the second arm. In some embodiments, at least a portion of each rod may be cylindrical in shape.

In one embodiment, an instrument is adapted for use in an anterior to psoas spinal access procedure. The instrument includes a body, a first arm attached to the body, a second arm attached to the body, a first rod attached to an end of the first arm remote from the body and a second rod attached to an end of the second arm remote from the body. The first rod is transverse to the first arm and the second rod is transverse to the second arm. The first rod includes a length with a first portion and a second portion, the first portion having a convex surface perimeter and the second portion having a perimeter different from the first portion and being convex in part.

In some embodiments, the instrument may include a pin holder having an engagement feature sized to engage with the first or second rod and may include a bone pin disposed therein. In some embodiments, the bone pin may protrude from each end of the pin holder. In yet some embodiments, the engagement feature of the pin holder may be a c-shaped channel. In yet some embodiments, the body may include a rack extending perpendicular to the first and second arms and one of the first and second arms may extend from a sleeve element enclosing a portion of the rack. The sleeve element may be adjustable relative to the rack in predetermined increments. In some embodiments, each of the first and second arms may be pivotable about an axis through the body. In some embodiments, the body may include two handles connected at a pivot point on the axis, each handle connected to a respective arm of the instrument such that movement of the handles with respect to each other causes a corresponding movement between the arms. In some embodiments, the first rod may be removable from the first arm and the second rod may be removable from the second arm. In some embodiments, one of the first rod and the second rod may include teeth engaged to an engagement feature of a respective arm. The teeth may be movable relative to the engagement feature in predetermined increments while engaged to the engagement feature so that the one of the first rod and the second rod is translatable along its longitudinal axis. In some embodiments, at least a portion of each rod may be cylindrical in shape. In some embodiments, the second portion of each rod may taper so that a first size of each rod remote from the first portion is larger than a second size of each rod adjacent to the first portion.

In another aspect, the present disclosure relates to a blade system for engagement with a bone surface. One embodiment of the blade system includes a blade and a pin. The blade has a length extending from a proximal end to a distal end and includes a convex outer surface and a concave inner surface. The concave inner surface has first, second and third grooves thereon. Adjacent to the distal end of the blade is a tapered tip portion. The pin of the system is disposed within the first or second groove of the blade.

In some embodiments, the first and second grooves may be offset from a longitudinal center of the blade on opposite sides of the longitudinal center and the third groove is coincident with the longitudinal center of the blade. In some embodiments, the tapered tip portion may be contoured to mate with a surface of an intervertebral disc. In some embodiments, the pin may include a head that prevents the pin from sliding through the blade when disposed therein, the head protruding from a proximal end of the first or second groove of the blade.

In some embodiments, the distal end of the blade may be a first distance from a plane through the first and second grooves and the third groove may be a second distance from the plane, the first distance being greater than the second distance. In some embodiments, the first groove may be located adjacent to a first lateral edge of the concave inner surface and may extend throughout a length of the concave inner surface and the second groove may be located adjacent to a second lateral edge of the concave inner surface and extend throughout the length of the concave inner surface.

In some embodiments, the third groove may include a first recess and a second recess within the first recess, the first recess being longer than the second recess. In some variants, the third groove may be sized for the disposal of a light bar therein.

In one embodiment, a system for engagement with a bone surface includes a principal blade and a pin. The principal blade includes a length with a main portion and an end portion and has a convex outer surface and a concave inner surface. The concave inner surface has first, second and third grooves thereon, the third groove being in between the first and second grooves. The pin is disposed within the first or second groove of the principal blade. The third groove of the principal blade is wider than each of the first groove and the second groove. Additionally, the third groove is adapted for receipt of at least one of an inner blade and a light bar. Further, the first groove and the second groove each have an axes therethrough such that a single plane passes through the respective axes and the end portion curves in a direction away from the single plane toward a terminal end of the end portion.

In some embodiments, the first and second grooves of the system may be offset from a longitudinal center of the principal blade on opposite lateral sides of the principal blade and the third groove may be coincident with a longitudinal center of the principal blade. In some embodiments, the end portion may be contoured to mate with a surface of an intervertebral disc. In some embodiments, the pin may include a head that prevents the pin from sliding through the principal blade when disposed therein. The head may protrude from a proximal end of the first or second groove of the principal blade. In some embodiments, the third groove may have a length longer than a length of the first groove. In some embodiments, the first groove may be located adjacent to a first lateral edge of the concave inner surface and may extend throughout a length of the concave inner surface and the second groove may be located adjacent to a second lateral edge of the concave inner surface and may extend throughout the length of the concave inner surface. In some embodiments, the third groove may include a first recess and a second recess within the first recess, the first recess being longer than the second recess. In some embodiments, the third groove may be sized for the disposal of a light bar therein.

In another aspect, the present disclosure relates to a kit for creating access to a surgical site. In one embodiment, the kit includes an instrument, a pin holder and a blade. The instrument includes two rods attached to a main body, while the pin holder is engageable to one of the rods. The pin holder includes a bone pin disposed therein. The blade has a length including a linear portion and a curved portion, the linear portion separating the curved portion from an engagement end of the blade. Each of the linear and curved portions has a concave surface that is continuous therebetween. When the instrument and the blade are inserted into a patient, the blade is oriented such that the concave surface faces the instrument to create a surgical access portal.

In some embodiments, when the pin holder is engaged to one of the rods, the bone pin of the pin holder may be parallel to the rod to which the pin holder is engaged. In some variants, the pin holder may include an enclosed passage therethrough sized for disposal of the bone pin therein. In some embodiments, the bone pin disposed in the pin holder may protrude from opposite surfaces of the pin holder.

In some embodiments, each rod of the instrument may be approximately perpendicular to the main body and have a cylindrical shape over part of its length. In some variants, each rod of the instrument may include an engagement mechanism adapted for releasable engagement with a corresponding engagement mechanism on the main body. In some embodiments, the distal portion of the blade may be curved in a direction such that no part of the blade extends beyond a plane through lateral edges of the concave surface of the central portion. In some embodiments, the distal portion of the blade may be tapered.

In one embodiment, a kit for creating access to a surgical site includes an instrument, a pin holder and a blade. The instrument includes two rods attached to a main body of the instrument. The pin holder is engageable to one of the rods and includes a bone pin disposed therein. The blade has a length including a linear portion and a curved portion. The curved portion defines an engagement end of the blade and curves out of a plane through opposing lateral edges of the linear portion, each of the linear and curved portions having a concave surface. The concave surface spans continuously between the linear and curved portions. When the instrument and the blade are inserted into a patient, the blade is oriented such that the concave surface of the blade faces the instrument to create a surgical access portal.

In some embodiments, when the pin holder is engaged to one of the rods, the bone pin of the pin holder may be parallel to the rod to which the pin holder is engaged. In some embodiments, the pin holder may include an enclosed passage therethrough sized for disposal of the bone pin therein. In some embodiments, the bone pin disposed in the pin holder may protrude from opposite surfaces of the pin holder. In some embodiments, each rod of the instrument may be approximately perpendicular to the main body and have a cylindrical shape over part of its length. In some embodiments, each rod of the instrument may include an engagement mechanism adapted for releasable engagement with a corresponding engagement mechanism on the main body. In some embodiments, the blade may include a distal portion curved in a direction such that the blade is entirely on one side of a plane through lateral edges of the concave surface of the central portion. In some embodiments, the distal portion of the blade may be tapered.

In another aspect, the present disclosure relates to methods of accessing a surgical site. In one embodiment, a method involves: Advancing a blade toward a spine of a patient using an anterior to psoas approach; directing a tip of the blade toward an intervertebral disc of the spine; advancing two rods of an instrument toward vertebrae adjacent to the intervertebral disc; and creating a surgical access portal by modifying the positioning of the blade and the two rods with respect to each other.

In some embodiments, the method may involve securing pins attached on respective ends of each of the two rods into respective vertebrae. In a variant, the method may involve, prior to the securing step, adjusting a position of one of the two rods relative to the other of the two rods by moving an arm holding the one of the two rods along a rack of the instrument connecting the rods. In some embodiments, directing the tip of the blade may involve directing a first blade component of the blade into the intervertebral disc, where the first blade component is disposed in a recess of a second blade component of the blade. When directed into the intervertebral disc, the first blade component extends distally from the second blade component.

In one embodiment, a method of accessing a surgical site includes: advancing a blade toward a spine of a patient using an anterior to psoas approach; directing a tip of the blade toward an intervertebral disc of the spine such that a surface of the blade is pressed against a surface of the intervertebral disc; advancing two rods of an instrument toward vertebrae adjacent to the intervertebral disc to create a surgical access portal; and altering a size of the surgical access portal by modifying the positioning of at least one of the blade and the two rods while the blade and the two rods are positioned adjacent to the spine.

In some embodiments, the method may also include securing pins attached on respective ends of each of the two rods into respective vertebrae. In some embodiments, prior to the securing step, a position of one of the two rods relative to the other of the two rods may be adjusted by moving an arm holding the one of the two rods along a rack of the instrument connecting the rods. In some embodiments, directing the tip of the blade may involve directing a first blade component of the blade into the intervertebral disc, the first blade component disposed in a recess of a second blade component of the blade and extending distally from the second blade component.

BRIEF DESCRIPTION OF THE DRAWINGS

The present disclosure will be better understood on reading the following detailed description of non-limiting embodiments thereof, and on examining the accompanying drawings, in which:

FIGS. 14-16 are various views of a double pin blade according to another embodiment of the disclosure.

DETAILED DESCRIPTION

Figure 1:
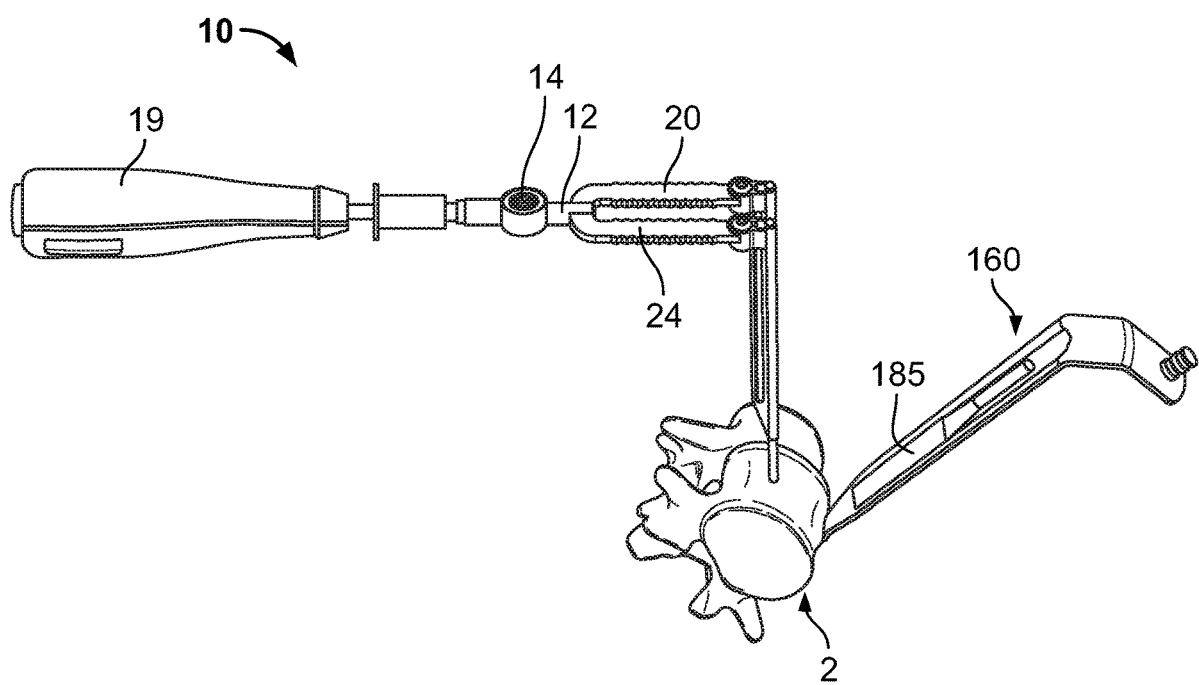
FIG. 1 is a perspective view of a retraction instrument and a blade positioned proximal to a spine, according to one embodiment of the disclosure.

Tools for accessing the spine using an anterior to psoas approach may include any number of retraction instruments and/or blades. For example, access to the spine 2 may be provided through a system that includes a retraction instrument 10 and blade 160 as shown in FIG. 1, where each structure is capable of reaching a surface of the spine and retracting tissue and other anatomy to create a surgical access portal so that a surgical site is accessible. Although each embodiment described herein makes reference to an anterior to psoas surgical approach, it is contemplated that the tools described herein may also be used in any number of other surgical procedures for the creation of access to a surgical site of a patient. For example, an anterior lumbar interbody fusion procedure (ALIF), or as known more generally as an anterior procedure, may also be used. We now turn to the details of the various tools used to create access to a surgical site.

Figure 2:
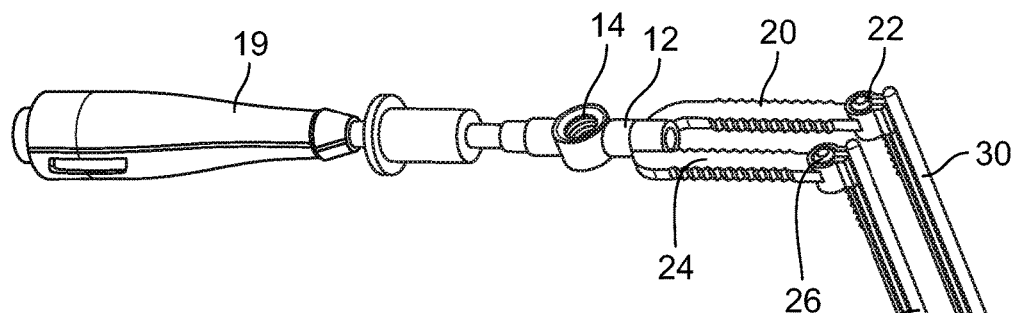
FIG. 2 is a perspective view of the retraction instrument shown in FIG. 1.

Retraction instrument 10 is shown in more detail in FIG. 2. Retraction instrument 10 includes a body 12 having arms 20, 24 extending in parallel therefrom on one end and an attachment mechanism 14 on another end. The attachment mechanism 14, one example of which is a universal quick release adapter, allows for engagement of body 12 with a handle 19, as shown in FIG. 1, or a rigid arm (not shown). One example of the attachment mechanism is the XIA 3 Quick Attachment by Stryker® and one example of the handle is the XIA 3 Quick Connect Handle by Stryker®. The rigid arm, if used, may be the same structure used in a lateral trans-psoas procedure. Each arm 20, 24 is rigidly connected to body 12 and includes an engagement feature 22, 26, respectively, at an end opposite its attachment to body 12. Rods 30, 34 are attached to the respective engagement features 22, 26 on the arms. The rods may be made of titanium or stainless steel, for example.

Figure 3:
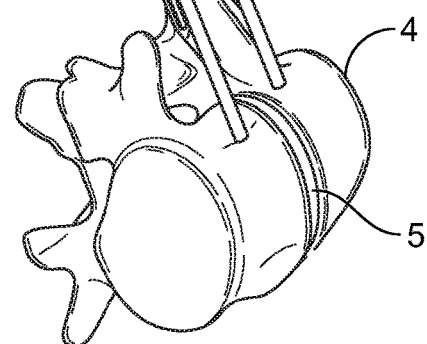
FIG. 3 is a side view of an arm and rod of the retraction instrument shown in FIG. 1.
Figure 3:
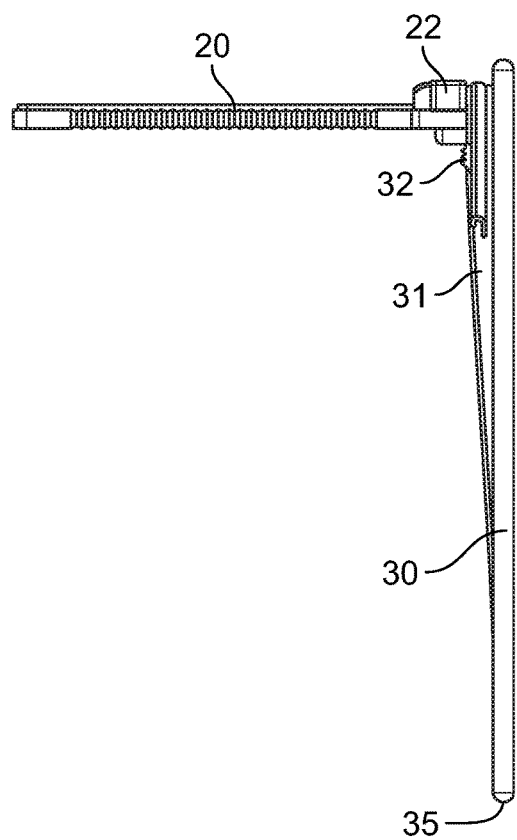

A more detailed view of one of the arms and rods is shown in FIG. 3. Rod 30 is cylindrical in shape with a rounded distal end 35 and is orthogonal to arm 20. In variants, the rod may be at another angle relative to the arm. It should also be noted that the rods are not limited to having a cylindrical shape, and that the rods may have another shape defined by a convex surface perimeter, or other shapes as described elsewhere in this application. A tapering structure 31 is attached on one side of each rod and faces the arm such that the tapering structure becomes larger toward the arm. Adjacent to a connection with arm 20, rod 30 includes teeth 32, spaced in a longitudinal direction and facing the arm. Within engagement feature 22 is a generally cylindrical threaded insert (not shown) that engages with teeth 32 to control a position of rod 30 relative to arm 20 along an axis through the arm in predetermined increments. The rods are removable from the arms by sliding the rod out of the engagement feature, and thus can be separated from an arm and reattached, as desired. In some alternatives, each of the engagement feature and the rod may include slots, dovetail connections, or other structures to facilitate attachment therebetween. Attachment of the rod to the arm may also be through other structural features described in U.S. Pat. App. Pub. No. 2019/0298328, the disclosure of which is hereby incorporated by reference herein in its entirety ("the '328 Publication").

Retraction instrument 10 is advantageous in that it includes retraction structures in the form of rods with perimeters defined by convex surfaces, e.g., cylindrically shaped, and occupying a minimal cross-sectional area. The size and shape of the rods reduces the interference of the retraction instrument with the operative space, allowing a surgeon to approach the surgical site from many angles and positions. Additional operative space is also made available in view of the space between the arms from the main body to the rods. Further, the rounded surface of the rods reduces the risk of damaging internal organs of the patient during advancement of the instrument. Moreover, each rod is engineered to withstand a certain amount of deflection under loading. Put another way, the properties of the rods provide sufficient elastic flexibility to withstand deflection that can result from tissue bearing on the rods during use without reaching yield under the highest loads expected within a body of a patient. The rods as described are also usable in a retractor adapted for use in a lateral trans-psoas approach, such as the retractors described in the '328 Publication. Because the rods may be detached and reattached, it is envisioned that rods already attached to the retraction instrument may be detached and then reattached to a lateral trans-psoas retractor.

Figure 6:
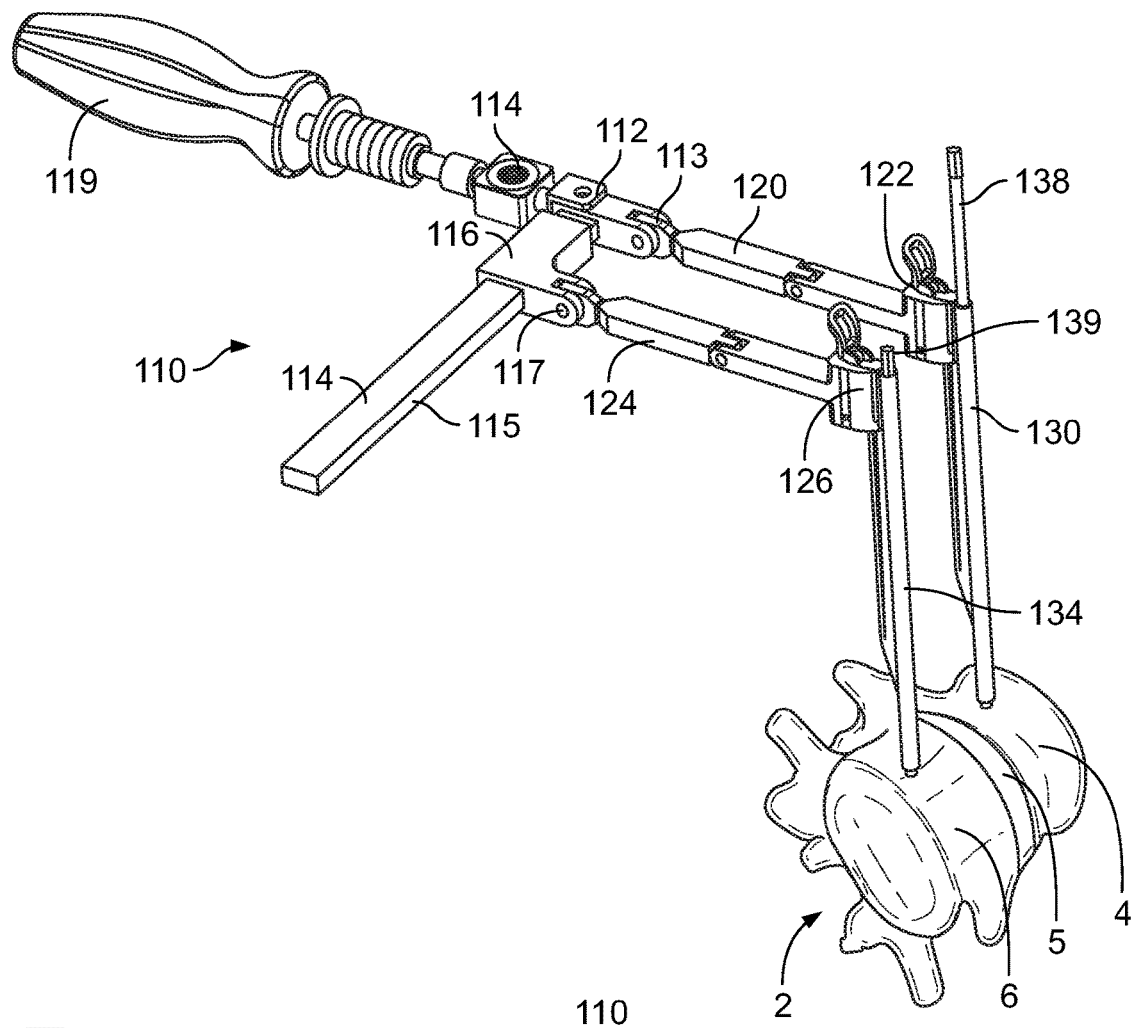
FIGS. 6 and 7 are perspective views of a retraction instrument according to one embodiment of the disclosure.
Figure 7:
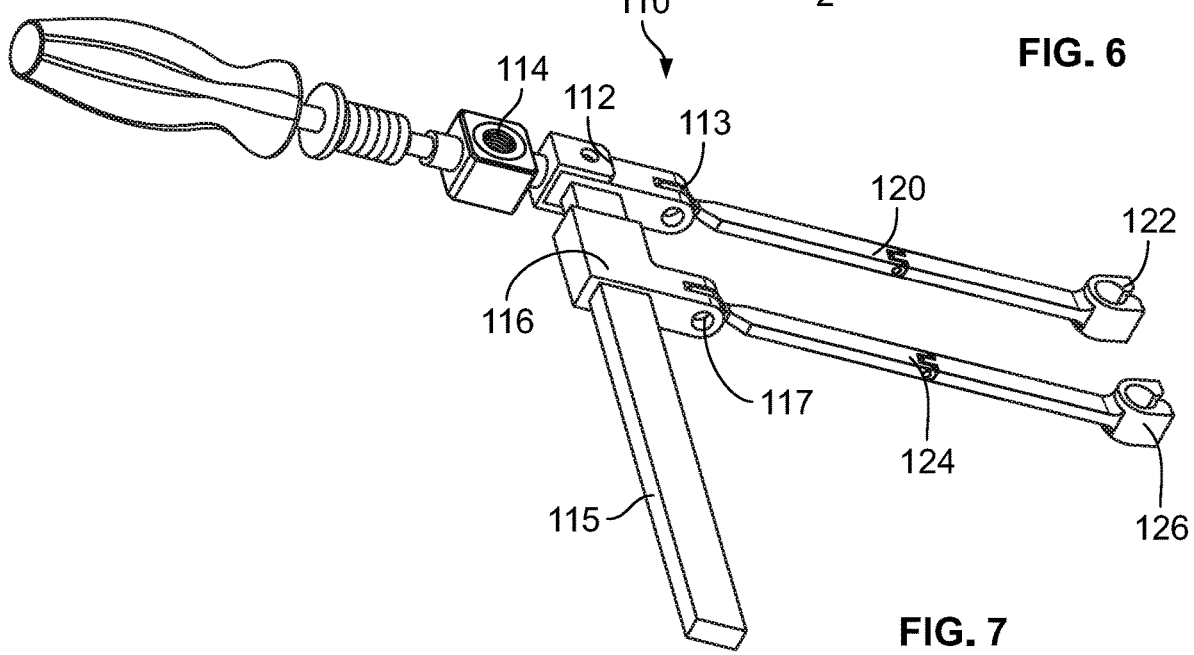

The retraction instrument may be varied in many ways. In one embodiment, a retraction instrument 110 is as shown in FIGS. 6 and 7. Unless otherwise noted, like reference numerals refer to like elements as shown in FIGS. 2 and 3. Instrument 110 includes a central body 112 with attachment mechanism 114 on a first side and a pivot structure 113 on an opposite side. As shown, a handle 119 is attached to attachment mechanism 114, although the handle may be replaced so that the instrument is secured by a rigid arm (not shown). Attached to central body 112 in a fixed manner is rack 114. As seen in FIGS. 6 and 7, rack extends orthogonally from a length of central body 112. In alternative variations, the rack may be oriented at another angle relative to the central body as a matter of design choice. Disposed over rack 114 is sleeve 116. Sleeve 116 is sized for a secure fit over rack 114. Rack 114 includes teeth 115 and sleeve includes corresponding teeth so that sleeve 116 is movable in predetermined increments along rack 114. In an alternative configuration, an engagement feature other than teeth may be used.

FIGS. 6 and 7 also show arm 120 extending from pivot mechanism 113 of central body 112 and arm 124 extending from a pivot mechanism 117 on sleeve 116. Arms 120 and 124 are parallel to one another and a distance between the arms may be between 12 mm and 15 mm, though the amount may vary as a matter of design choice. Because arm 124 is secured directly to sleeve 116, movement of sleeve 116 relative to central body 112 along rack 114 correspondingly moves rod 134 relative to rod 130, as shown in FIG. 6. In this manner, retraction instrument 110 provides for an adjustable retracted surgical access portal. The pivot mechanisms 113, 117 as shown provide fixed securement of the arms to the body and rack, respectively. Alternatively, the arms may be adjustable relative to the body such that the arms are locked in a desired position relative to the central body and rack. For example, an angle between a length of one or more arms relative to a plane passing through both the central body and rack may be adjusted by rotating the arm about the pivot mechanism.

Turning to the rods used with the retraction instrument, in one example, as shown in FIG. 6, each rod 130, 134 includes a cannulation therethrough. The cannulations through such rods are sized for the disposal of threaded pins 138, 139 therein. As shown in FIG. 6, the pins are engageable with vertebral bodies 4, 6 when positioned in a patient. These rod variations may also be used with other embodiments of the retraction instrument described and otherwise contemplated elsewhere in the disclosure.

Figure 8:
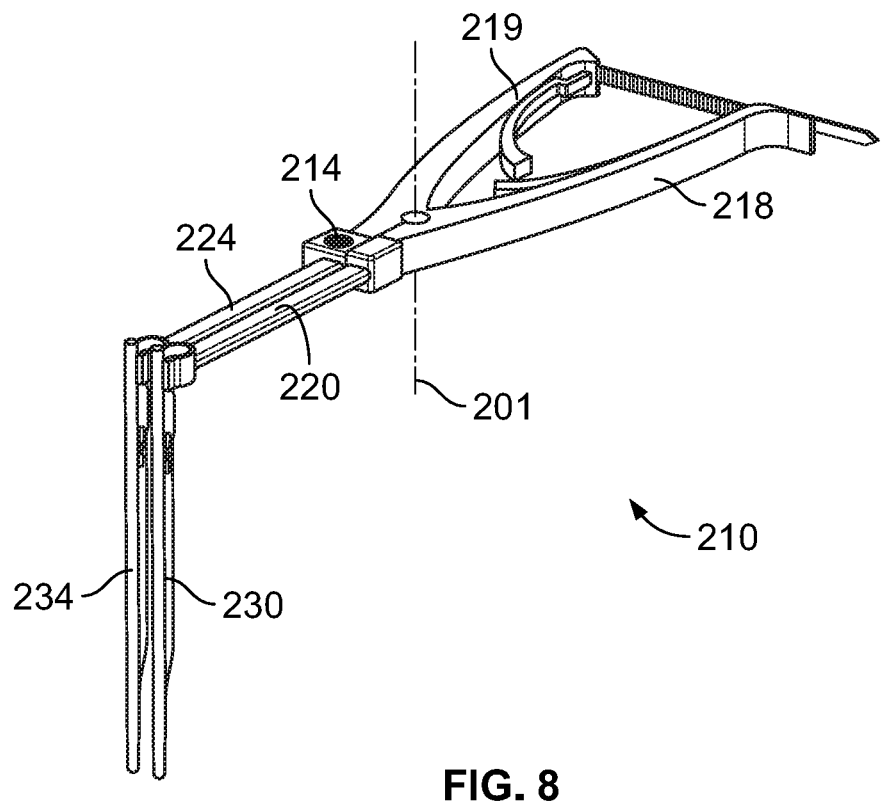
FIGS. 8 and 9 are perspective views of a retraction instrument according to another embodiment of the disclosure.
Figure 9:
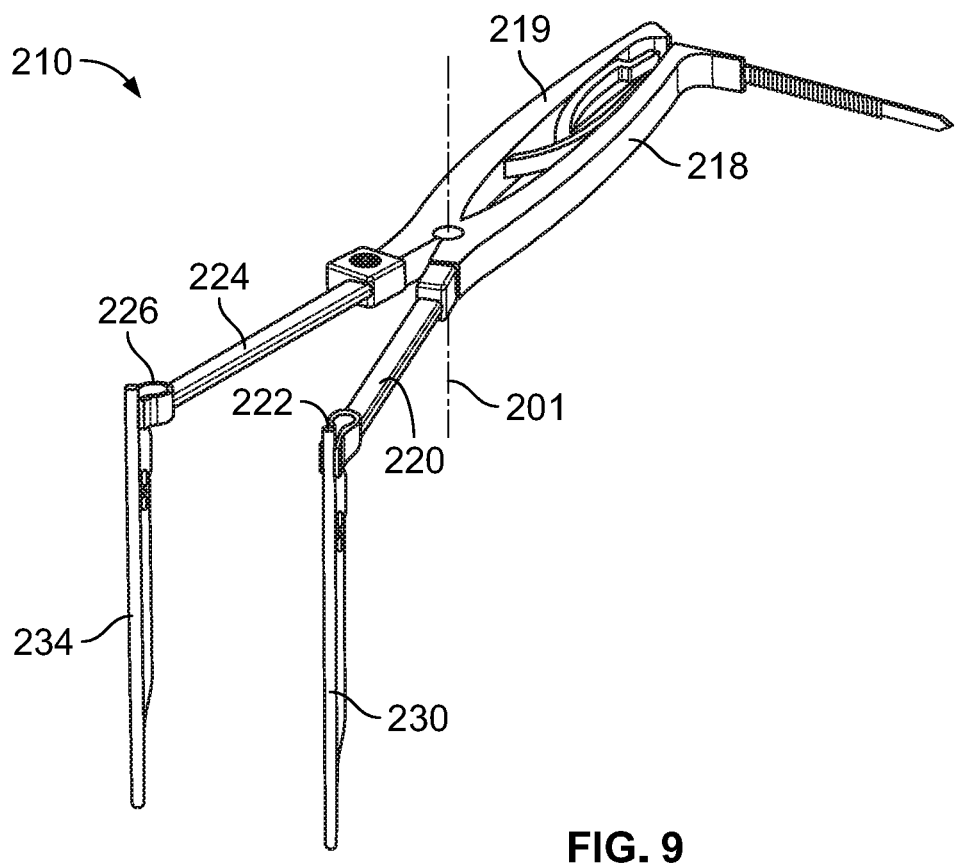

In one embodiment, a retraction instrument 210, shown in FIGS. 8 and 9, includes handles 218, 219 attached to respective arms 220, 224. At an end of each arm 220, 224, a rod 230, 234, is attached. Unless otherwise noted, like reference numerals refer to like elements as shown in FIGS. 2 and 3. Handles 218, 219 are pivotable with respect to one another and are connected at a location on a pivot axis 201. When handles 218, 219 are brought closer together, as shown comparing FIG. 8 to FIG. 9, distal ends of arms 220, 224 and attached rods 230, 234 move away from one another. Adjacent to an interface between arm 224 and handle 219, arm 224 includes an attachment mechanism 214 for securement of retraction instrument 210 to a rigid arm. In a variation, the handle and arm combination may be arranged like scissors, so that each handle is connected to an arm on an opposite side. In this manner, closing of the handles brings the rods closer together while opening of the handles spreads the rods further apart.

In some examples of the retraction instrument, the attached rods may have an oblong, elliptical, ovular or any other cross-sectional shape as desired. In other examples, one or more of the rods may have a pointed tip shaped to engage bone upon loading thereon. Retraction instruments including such rods may be secured to a bone without a separate anchoring structure.

Further examples of rod shapes and other rod details are provided in the '328 Publication, incorporated by reference above, and in WO2018/039228, the disclosure of which is hereby incorporated by reference herein in its entirety ("the '228 Publication"). In some examples, the body, arms and/or rods may be comprised of a monolithic structure in whole or in part. Thus, the body and arms may be a monolithic structure or an arm and a rod connected to the arm may be a monolithic structure. Further, the body, arms and rods may all be a single monolithic structure. In other examples, various combinations of the body, arms and rods may be integral. In further examples, a length of a body of a retraction instrument may be at an angle relative to a length of one or more arms attached thereto. Similarly, where the retraction instrument includes a rack, the rack may be at any angle relative to the central body and/or one or more of the arms. The angle between elements in these examples may be such that all structures are in a single plane or one or more structures may be angled out of plane with respect to the others. For example, a retraction instrument may include two arms passing through a single plane while the main body and handle extend at an angle from the arms out of the single plane. Similar variations are contemplated for an angle between the rods and the arms. And, a length of a first arm may be at an angle relative to a length of a second arm.

In other examples, a first rod on a retraction instrument may be different from a second rod. Any combination of the rods described in the '328 Publication and the '228 Publication may be included. In still further examples, the retraction instrument may include three or more rods with corresponding arms. The rod and arm combinations may be parallel with one another or one or more may be at an angle relative to the others. In yet another example, the rods may be attached to a single body without any arms.

Figure 4:
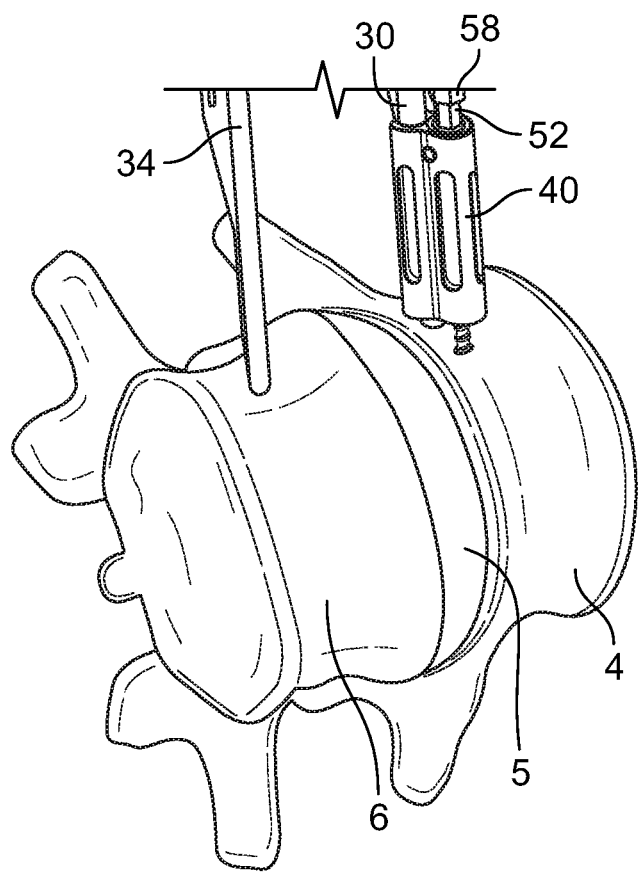
FIG. 4 is a close up perspective view of the rods of the retraction instrument shown in FIG. 1 with a pin holder attached to one of the rods and a vertebral body, according to one embodiment of the disclosure.
Figure 5:
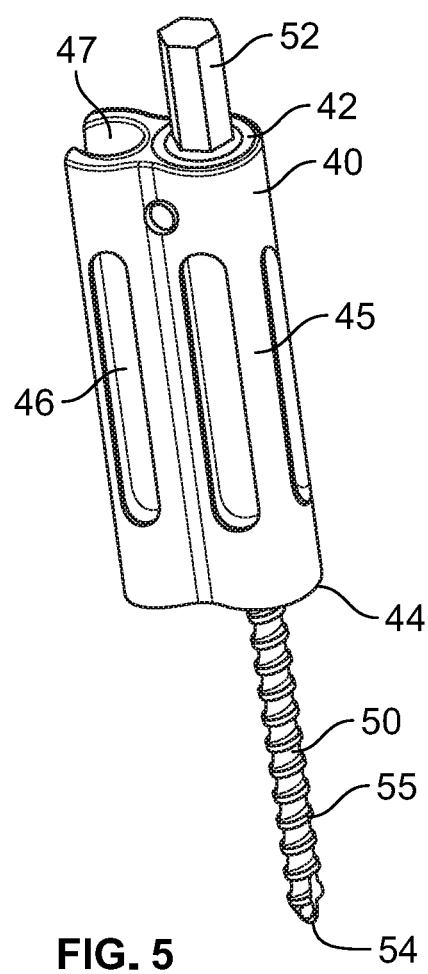
FIG. 5 is a perspective view of the pin holder shown in FIG. 4.

In another aspect, the present disclosure relates to a pin holder 40 as shown in FIGS. 4 and 5. Pin holder 40 includes a cylindrical component 45 and a partially cylindrical component 46 that is monolithic with the cylindrical component. However, in an alternative configuration, the partially cylindrical component may be a separate structure attached to the cylindrical component. The cylindrical component includes an internal channel therethrough sized for the disposal of a bone pin. In FIG. 5, bone pin 50 is disposed within cylindrical component 45 of pin holder 40. Partially cylindrical component 46 includes a groove 47 therethrough to define a c-clip structure. As shown in FIG. 4, groove 47 is sized to accommodate rod 30 of retraction instrument 10 therein. Groove 47 is parallel to the internal channel of the cylindrical component such that when pin holder 46 is attached to a rod, for example, bone pin 50 disposed within pin holder 40 is parallel to the rod. The c-clip of partially cylindrical component 46 provides a friction fit to an element engaged thereto.

The pin holder is advantageous in that it adds a bone securement feature to retraction instrument 10, 110, 210 and it is insertable after a portal is created to avoid having to pass a pointed tip on the bone pin of the pin holder through anatomy of the patient. Further, the position of the internal channel offset from the c-clip structure allows a surgeon to screw in a bone pin while the pin holder is engaged to a rod.

In another aspect, the present disclosure relates to blades. One embodiment of a blade is a double pin blade 60 shown in FIGS. 10 and 11. Double pin blade 60 includes a proximal portion 61, central portion 62 and a tapered distal portion 63. Proximal portion 61 extends at an angle relative to central portion 62 and includes an opening (not shown) for engagement to a handle or a rigid arm via an attachment mechanism.

Figure 10:
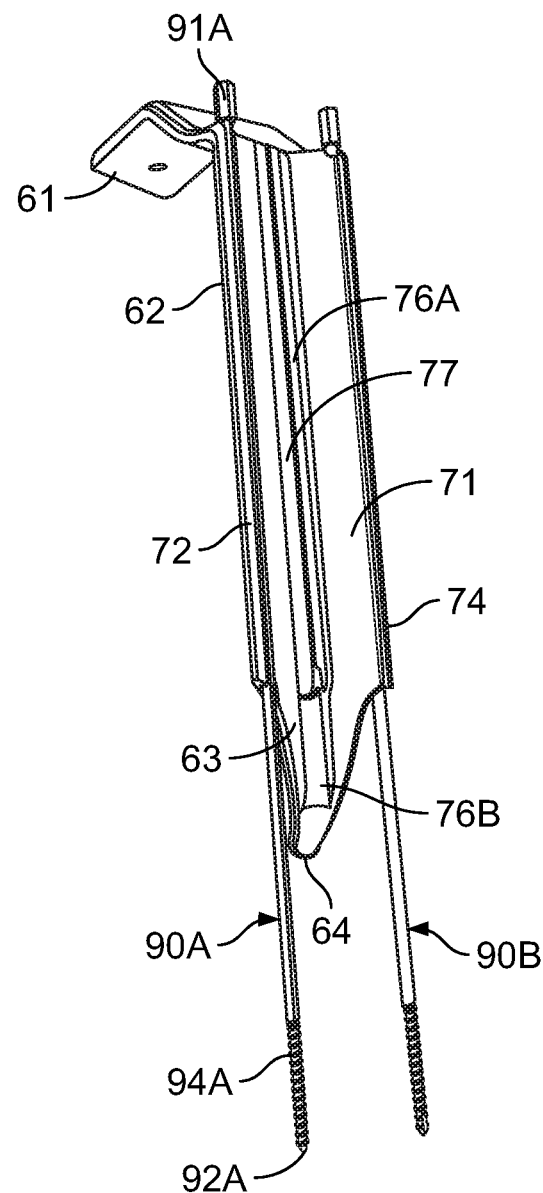
FIGS. 10 and 11 are views of a double pin blade according to one embodiment of the disclosure.

Turning to central portion 62, central portion 62 has a linear length with a concave surface 71 on one side and a convex surface 81 on an opposite side. On opposite lateral sides of concave surface 71 are longitudinally extending first and second lateral grooves 72, 74, respectively, as best shown in FIG. 10. Lateral grooves 72, 74 are nearly enclosed in their entirety, although in variants, a forward facing opening in the grooves may be wider or narrower than shown in FIG. 10. Each lateral groove is sized for the disposal of a bone pin 90A, 90B therein. Coincident with a central longitudinal axis of double pin blade 60 on central portion 62 is a central recess including an upper central recess 76A, 76B and a lower central recess 77 that is recessed relative to the upper central recess 76A. Through central portion 62 of double pin blade 60, upper central recess 76A is wider than lower central recess 77, each having a generally constant width along the central portion. Within the recesses, the surface of the blade is relatively flat compared to the convex curvature between the upper central recess and opposing lateral grooves. The various recesses in the blade are sized to accommodate disposal of a light emitting structure therein.

Figure 11:
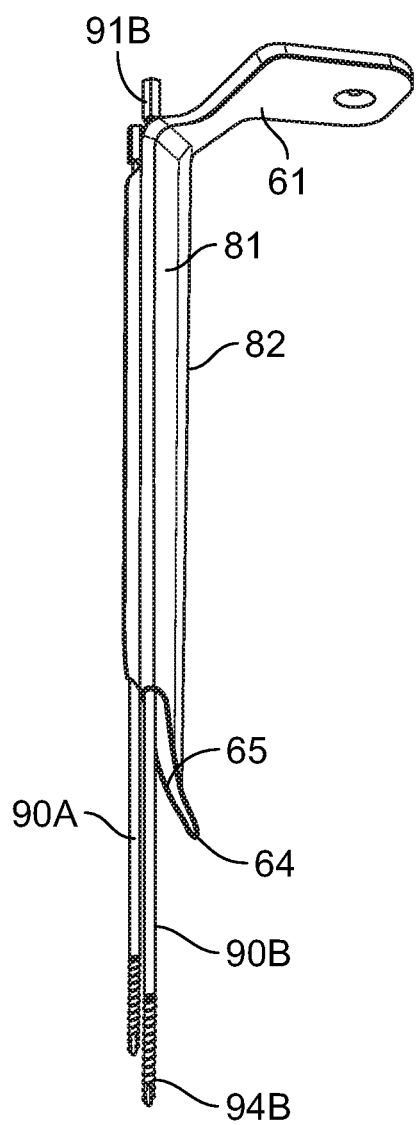

Tapered distal portion 63 extends from central portion 62 to a rounded tip 64 of the blade. As shown in FIG. 10, lower central recess 77 terminates near a distal end of central portion 62 and only upper central recess 76B extends toward tip 64. Upper central recess 76B is slightly narrower than upper central recess 76A. As shown in FIG. 11, as blade 60 tapers toward tip 64, it curves away from a plane through the first and second lateral grooves 72, 74. This curvature is indicated by reference numeral 65 in FIG. 11. It should also be noted that the surface on distal portion 63 extending from concave surface 71 on central portion 62 is also concave.

Opposite concave surface 71 is convex surface 81, as shown in FIG. 11. Convex surface 81 is interrupted on a central axis by a longitudinally extending central ridge 82 corresponding to upper and lower central recesses 76A, 76B, 77. Since concave surface 71 and convex surface 81 are opposing surfaces on blade 60, a cross-section through double pin blade 60 is defined by a generally arcuate shape.

In another embodiment, a system includes double pin blade 60 and pins 90A, 90B. Pin 90A includes a cylindrical body extending from a head 91A to a tip 92A. A majority of a length of pin 90A includes a smooth surface, although a distal end portion 94A extending to tip 92A is threaded. Pin 90B is the same as pin 90A. In the system, each pin 90A, 90B is disposed in respective first and second lateral grooves 72, 74, as shown in FIGS. 10 and 11. In a variant, a system may include a single pin along with a double pin blade.

Double pin blade 60 is advantageous in that it is adapted to house up to two pins for securement of blade 60 to a bone structure. Indeed, when two pins are used to secure blade 60 to a bone structure, both rotational and axial securement are realized. Further, blade 60 includes a contoured tip 64 to improve surface area contact with curved surfaces, such as those on the spine.

Figure 12:
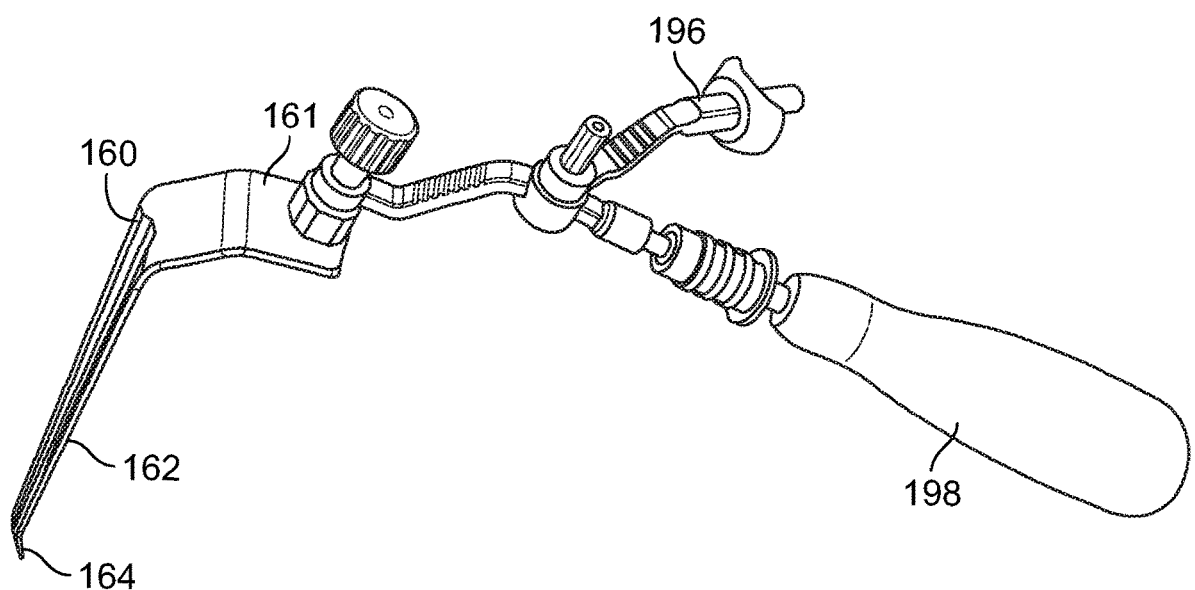
FIG. 12 is a perspective view of another embodiment of a blade attached to a handle.
Figure 13:
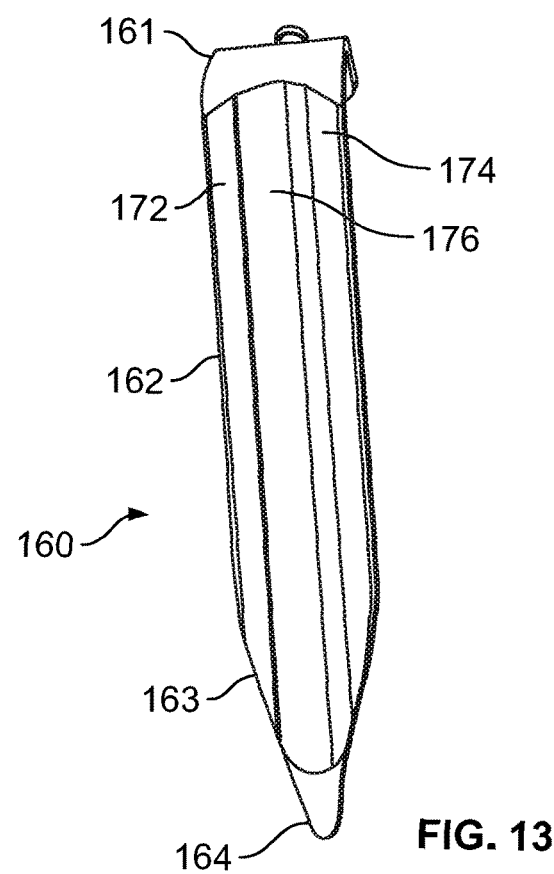
FIG. 13 is a perspective view of the blade shown in FIG. 12.

In another embodiment, blade 160 is as shown in FIGS. 12 and 13. Unless otherwise noted, like reference numerals refer to like elements as shown in FIGS. 10 and 11. Blade 160 includes a proximal portion 161, a central portion 162 and a tapered distal portion 163. Proximal portion 161 is angled relative to central portion and includes an opening for engagement with an attachment mechanism 196. As shown in FIG. 12, the attachment mechanism 196 is connected to handle 198, although in other variants, attachment mechanism may be connected to a rigid arm. As shown in FIG. 13, central portion 162 includes a concave surface with two lateral portions 172, 174 separated by a recessed portion 176. A surface opposite the concave surface is convex (not shown). Distal to central portion 162 and extending to a tip 164 of blade 160 is tapered portion 163. Tapered portion is curved so that a surface on the tapered portion retreats in a direction away from a plane through respective lateral edges of blade 160 toward tip 164, as shown in FIG. 12. An extreme end of tip 164 is rounded. In a variant, a light emitting structure 185 may be secured onto recessed portion 176 with adhesive backed tape, for example, as shown in FIG. 1. Other forms of securement are also contemplated, which may be chosen as a matter of design choice. This light emitting structure provides light directed to the distal tip of blade 160.

In yet another embodiment, a double pin blade 260 is as shown in FIGS. 14-16. Unless otherwise noted, like reference numerals refer to like elements as shown in FIGS. 10 and 11. Double pin blade 260 includes a central portion 262 with a convex surface 271. Similar to double pin blade 60, concave surface 271 includes first and second lateral grooves 272, 274 and centrally located upper and lower central recesses 276A, 276B, 277. A plane 269 passes through both lateral grooves 272, 274. Distal portion 263 of blade 260 is not tapered but does curve away from plane 269. In particular, for example, lateral edges 265, 266, as shown in FIGS. 14 and 16, become further from plane 269 toward distal end 264. A surface between lateral edges 265, 266 is concave on the same side of blade 260 as concave surface 271. Also visible in FIG. 16, distal end 264 has a rounded edge.

Figure 17:
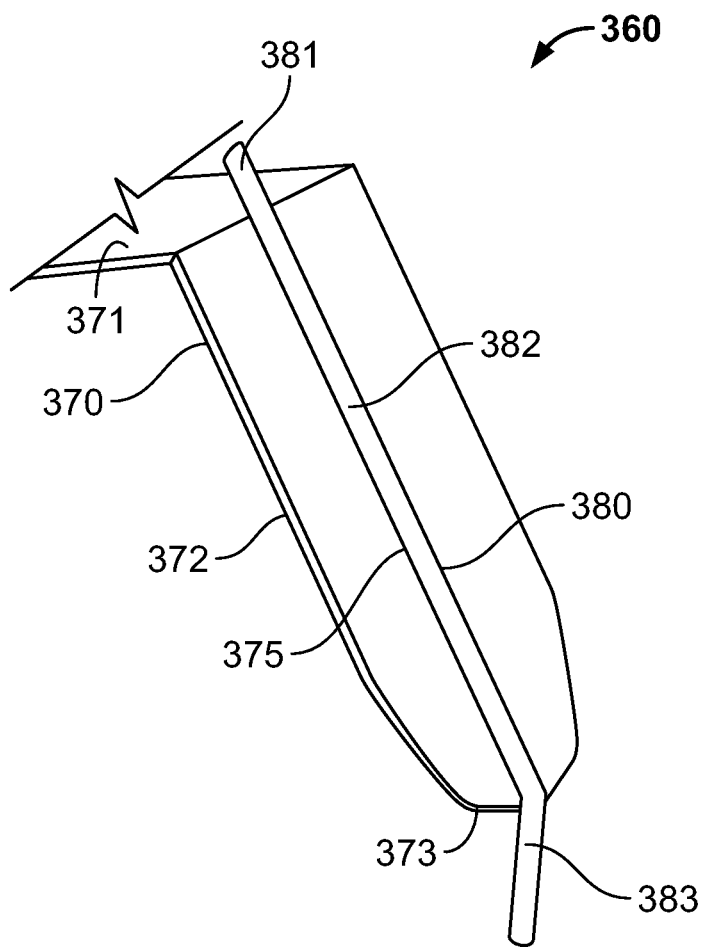
FIG. 17 is a perspective view of a composite blade according to another embodiment of the disclosure.

In yet another embodiment, the present disclosure relates to a composite blade 360 that includes an outer blade component 370 and an inner blade component 380. Inner blade component 380 is narrower than outer blade component and is engageable with a groove 375 in outer blade component 370, as shown in FIG. 17. In one example, outer blade component is 25 mm wide while inner blade component is 5 mm wide. Inner blade component is at least partially linear 382 and is engageable with outer blade component 370. For example, a surgeon may clip inner blade component 380 onto outer blade component 370. A distal end portion 383 of inner blade component 380 is angled and has surface contours to suit contact with a curved surface, such as a vertebral body or intervertebral disc. Once attached to outer blade component 370, inner blade component 380 may be removed and reattached as desired. It should be appreciated that an inner blade component such as inner blade component 380, may also be sized for receipt in other blades of the disclosure, including, for example, double pin blade 60.

Figure 24:
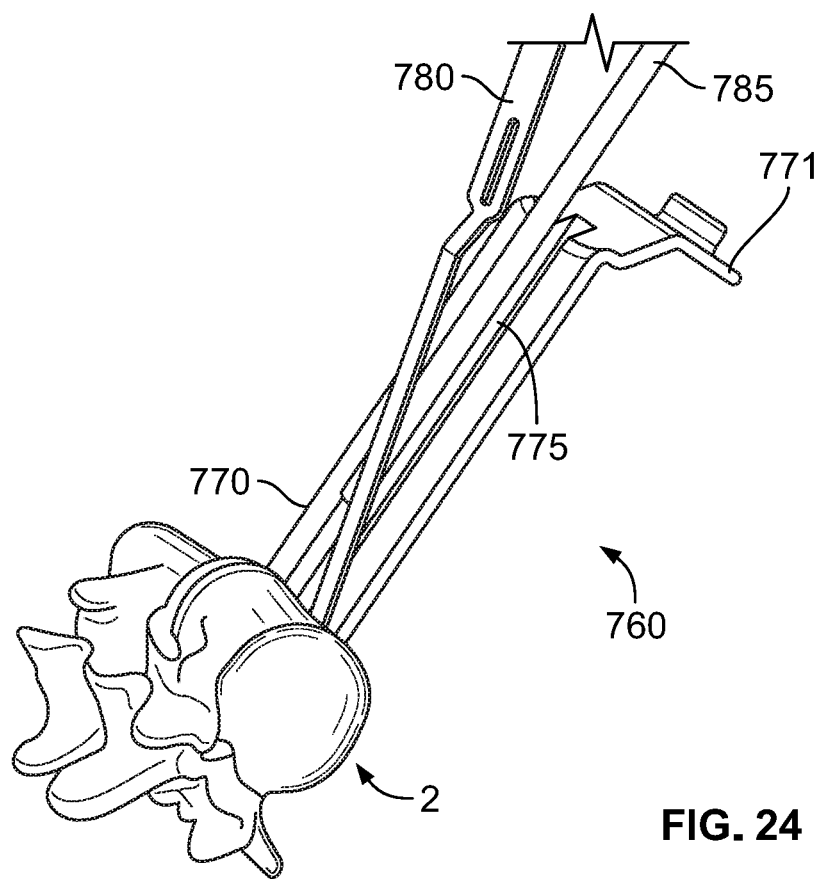
FIGS. 24 and 25 are views of a composite blade according to another embodiment of the disclosure.
Figure 25:
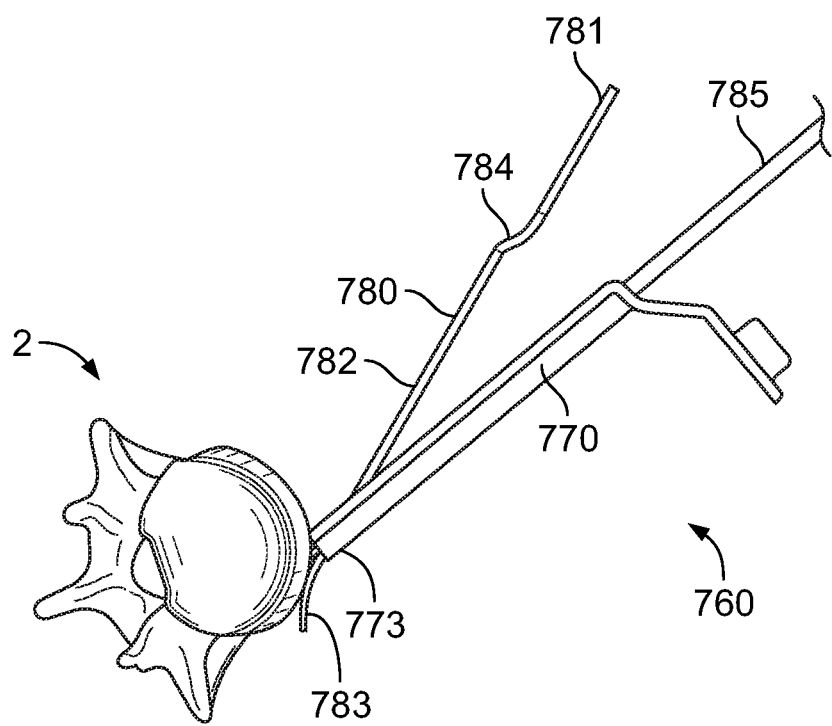

Another embodiment of the composite blade is shown in FIGS. 24 and 25. Unless otherwise noted, like reference numerals refer to like elements as shown in FIG. 17. Composite blade 760 includes an outer blade component 770 and a light bar 785 which is engageable with a groove 775 in outer blade component 770. Engagement of the elements is through a snap fit connection so that light bar 785 may slide within groove 775, though the form of engagement may vary as a matter of design choice. Composite blade also includes inner blade component 780, which may be independently operated with respect to outer blade 770, though it is sized to fit along groove 775 to guide a position of a curved distal portion 783. Inner blade component 780 also includes a bent segment 784 toward a proximal end 78. Curved distal portion 783 and bent segment 784 are separated by a linear central portion 782. Curved distal portion 783 and bone segment 784 both extend in the same direction away from a plate through central portion 782, as shown in FIG. 25.

Figure 18:
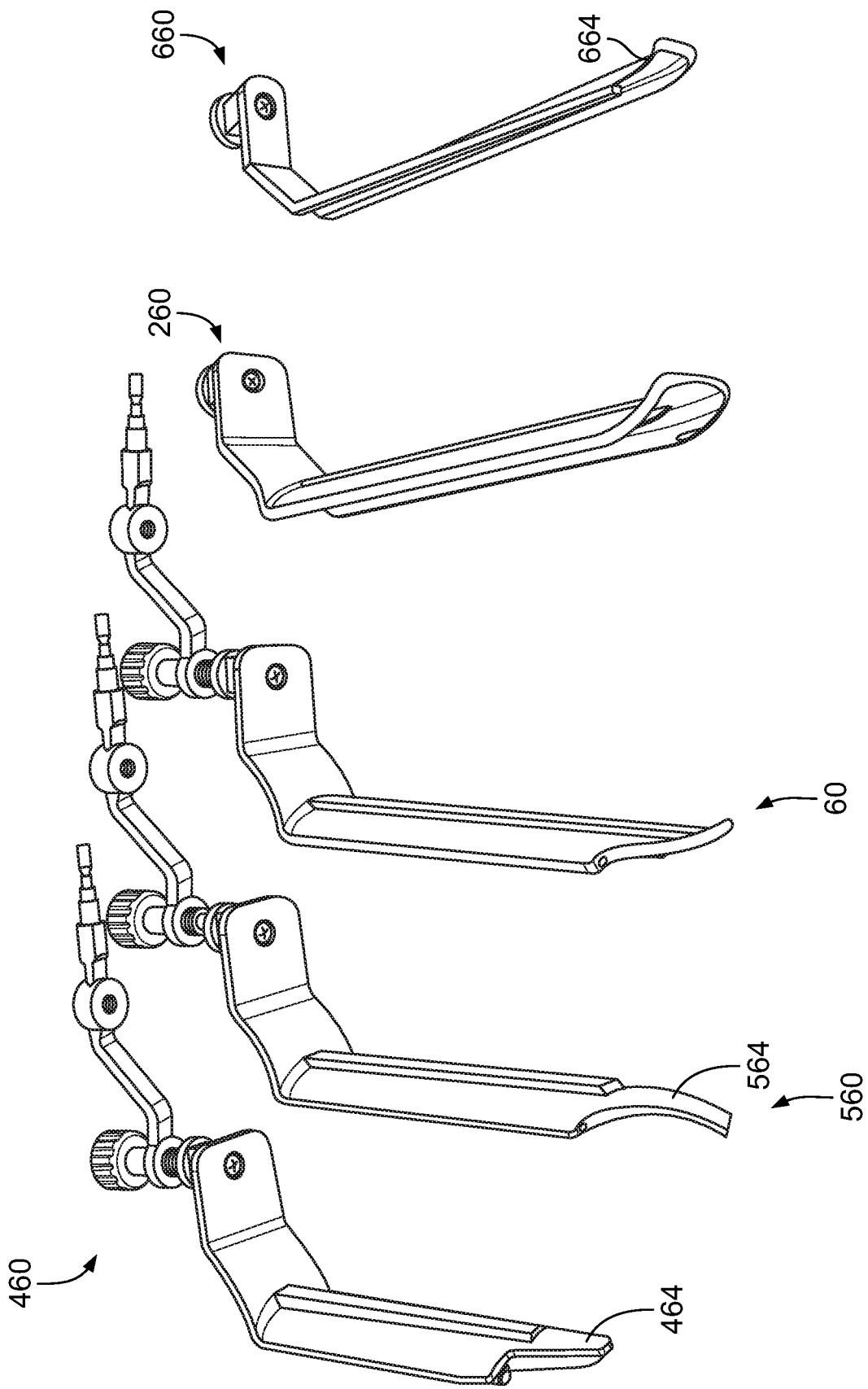
FIG. 18 is a perspective view of several different blades, each representing a different embodiment of the disclosure.

The blade may be varied in many ways. Additional examples of blades, along with another view of blades 60 and 260, are illustrated in FIG. 18. Blade 460 includes a linear taper 464 sloped away from a plane through the lateral edges of the blade. Blade 560 includes a tapered portion 564 that is sloped toward a plane through the lateral edges. Blade 660 is a smaller blade having a curved distal portion. It is also contemplated that the blade may be varied to suit particular surgical needs. For example, the radius of the surface across the width of the blade may be greater or less than that shown in the figures. In other examples, the length or width of the blade may vary to suit particular circumstances.

In another aspect, the present disclosure relates to a kit. A kit may be contained in a single package as a system or in multiple packages that may be selected as needed by a surgeon to form a system. In one embodiment, a kit includes a retraction instrument and a blade. When referred to as part of a kit, a blade may be any blade described or otherwise contemplated in this disclosure. In another embodiment, a kit includes a retraction instrument and two or more blades. Any combination of blades may be included, either multiple blades of the same type, or different blade types. In yet another embodiment, a kit includes two or more retraction instruments and a single blade. When two or more retraction instruments are included, each instrument may be the same or may be different. In further embodiments, a kit may include two or more retraction instruments without any blades or may include two or more blades without any retraction instruments. In each of the above embodiments, the kit may also include multiple units of a single type of blade but in different sizes. It is also contemplated that the above kits may be further modified to include other surgical tools used in conjunction with the retraction instrument and blades. In some examples of the above embodiments, the kits contemplated herein may be accompanied by an instruction manual on how to perform one or more of the methods of using the contents of the kit.

In yet another embodiment of the kit, tools of the described anterior to psoas system are included as part of a larger kit including a lateral trans-psoas system, such as the system and subcomponents described in the '328 Publication. In some examples, such a kit includes a lateral trans-psoas retractor system, an anterior to psoas retraction instrument with two arms and two rods and a composite blade. In other examples, it includes a lateral trans-psoas retractor system and any combination of anterior to psoas tools as described in the other kit embodiments above. The lateral trans-psoas retractor system forming part of the kit may include any number of components and tools described in the '328 Publication.

In another aspect, the present disclosure relates to a method of accessing the spine using an anterior to psoas approach. As noted above, although the specific embodiments described herein are directed to procedures employing an anterior to psoas approach, other procedures, such as an ALIF procedure, are also contemplated. Prior to commencement of the surgical technique using the tools of the present disclosure, preparation of the patient is required. These preliminary steps include but are not necessarily limited to: Positioning the patient; identifying an incision location based on the targeted spinal location; and cutting through muscle layers to create an opening for accessing spine. In an anterior to psoas approach, external oblique, internal oblique, transversus abdominus and transversalis fascia tissues are penetrated to create an initial opening, or initial portal, so that the surgeon may identify the psoas muscle and/or other anatomy and use such anatomy to locate the spine. In certain examples, the techniques described herein may be used to access vertebrae at L3/L4, L4/L5 and L5/S1.

Figure 19:
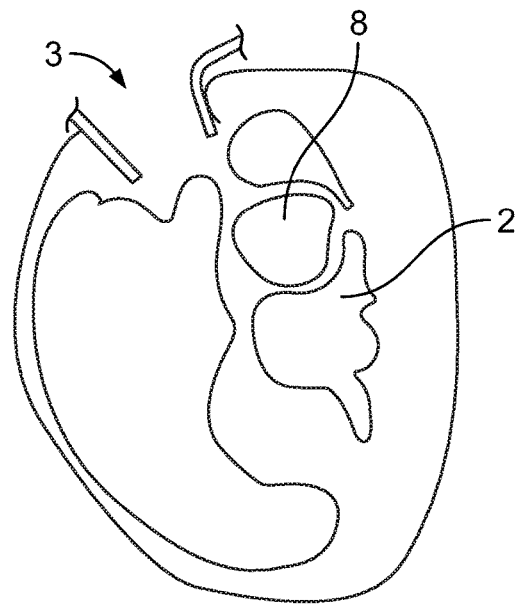
FIGS. 19-22 show steps in an anterior to psoas surgical technique performed according to one embodiment of the disclosure.
Figure 20:
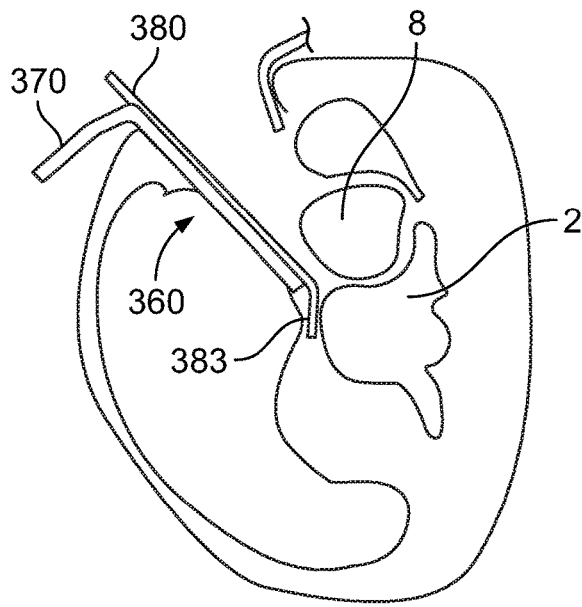

In one embodiment, with an initial portal 3 opened that is large enough so that tools may be advanced into the patient, as shown in FIG. 19, an outer blade component 370 of a composite blade 360 is advanced into the patient using an anterior approach to the spine on one side of the initial portal 3. During advancement of blade component 370, certain anatomy may be retracted medially including the peritoneum. Once outer blade component 370 is advanced close to the spine, inner blade component 380 is clipped onto groove 375 on outer blade component 370 and blade component 380 is slid down the groove so that a distal portion 383 is advanced beyond end 373 of outer blade component 370 until it is in contact with the spine and it otherwise retracts or protects the vessels from the spine, as shown in FIG. 20. The contours of the distal portion 383 of inner blade component 380 are then used to identify a position where contact between distal portion 383 and the intervertebral disc is maximized. In this manner, composite blade 360 is stabilized on the disc. At this time, a position of blade 360 may be preserved by manually holding a handle, or blade 360 may be secured to a fixed structure using a rigid arm (not shown).

Figure 21:
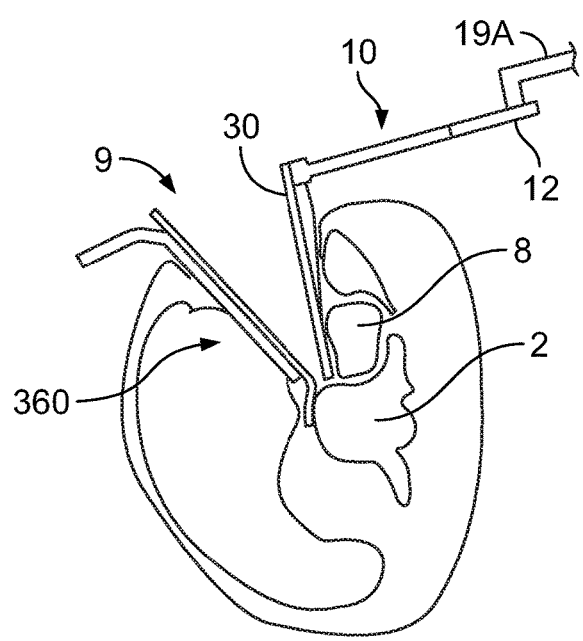
Figure 22:
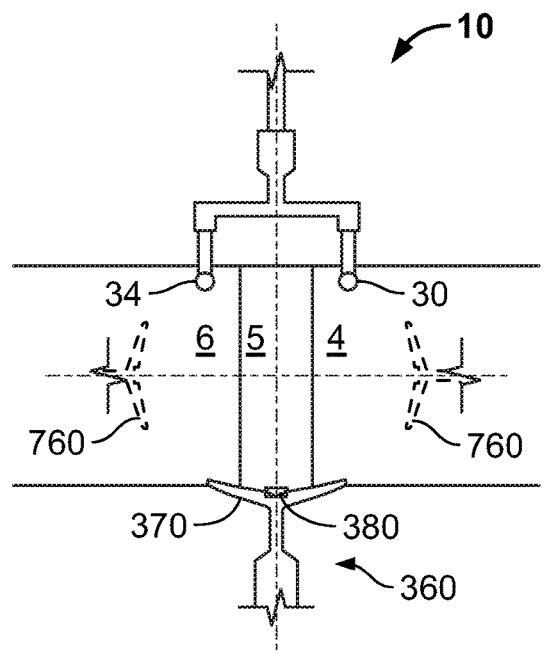

With blade 360 in position, rods 30, 34 of retraction instrument 10 are directed to an opposite side of the partially retracted opening from blade 360, as shown in FIG. 21, and then advanced into the patient using an antero-lateral approach. Because rods 30, 34 have rounded outer surfaces, the risk of damaging internal organs during the advancement of the rods is minimized. Once rods 30, 34 are in position adjacent to the spine, as shown in FIG. 21, retraction instrument 10 is either held in place or secured with a rigid arm 19A. The advancement of the rods retracts anatomy behind the rods, including psoas muscle 8 among other anatomical structures, creating a surgical access portal 9, shown in FIG. 21, for use by the surgeon to prepare a target intervertebral disc, place an implant or perform another task requiring access to the spine. In position, the respective rods 30, 34 are positioned directly over adjacent vertebral bodies 4, 6, as shown in FIG. 22. In some examples, either one or both of blade 360 and retraction instrument 10 may be further retracted at this time to increase the size of the surgical access portal or otherwise adjust its shape. FIG. 22 illustrates the position of the retraction instrument and blade at this stage of the procedure. Once the rods and blades are in position, the intervertebral disc 5 is accessible for the applicable surgical procedure.

Because rods 30, 34 of retraction instrument 10 retract tissue but are also spaced apart, and because arms 20, 24 are spaced apart, retraction instrument 10 provides a unique advantage in that a surgeon has more space to operate once surgical access portal 9 is created. For example, if the surgeon attaches an implant onto an insertion instrument, the surgeon may direct the instrument in between the rods or at steeper angles relative to the surgical access portal than would otherwise be possible with a traditional blade. Similar advantages are available for the insertion of disc preparation instruments.

Optionally, additional blades 760, shown in phantom in FIG. 22, may also be advanced into the surgical access portal and retracted to further increase the size of the surgical access portal or to adjust its shape.

In some variations of the method added stability, i.e., rigidity, is provided by attaching a pin holder 40 to one of the rods, such as the pin holder shown in FIG. 5, and sliding it down the rod so that a bone pin 50 disposed within the pin holder is in contact with or otherwise adjacent to a surface of a vertebral body. It should be noted that as pin holder 40 is advanced, the c-clip provides a friction fit with the rod so that the pin holder may be positioned at any desired location along the length of the rod and remain in that position. The sliding step may be performed by attaching a longitudinally extending driver instrument (shown in part as reference numeral 58 on FIG. 4) to the pin holder and then using a handle on the driver instrument to push down the pin holder. Driver instrument 58 includes an end opening shaped to mate and fit securely with head 52 of the bone pin so that the bone pin may be advanced. Because drive instrument 58 has an extended handle, the surgeon may continue to hold the driver instrument at a location external to the patient even when pin holder 40 is advanced toward a vertebra. One example of the driver instrument is the driver included as part of the ARIA System by Stryker®. To secure the bone pin to a bone beneath it, head 52 of bone pin 50 is actuated to drive a threaded portion 55 of the bone pin into the bone.

As the bone pin is rotated and advanced, the pin holder remains attached to the rod. Because the rod of the retraction instrument is attached to the pin holder, once the bone pin is secured to the bone, the retraction instrument is also secured to the bone. This bone anchoring step may also be performed on the other of the two rods so that both rods 30, 34 are secured to bone. When both rods are secured with bone pins, both rotational and axial securement of the retraction instrument are realized. Additionally, for subsequent surgeries, the bone pin in the pin holder may be replaced.

In another embodiment, the steps of the surgical technique are the same as those used to create the surgical access portal defined by the instrument and blade shown in FIG. 22, although retraction instrument 110 is used in place of retraction instrument 10. In this variation, once the rods of retraction instrument 110 are in position over the bone, sleeve 116 is adjusted to control a distance between the rods. This may be done to ensure that each rod is over the proper location on a vertebral body, for positioning of the rod so that an attached bone pin in a pin holder will properly engage the vertebral body, or for modification of the size or position of the surgical access portal. In yet another embodiment, similar principles apply to use of retraction instrument 210 to adjust positions of rods 230, 234 with respect to each other.

Figure 23:
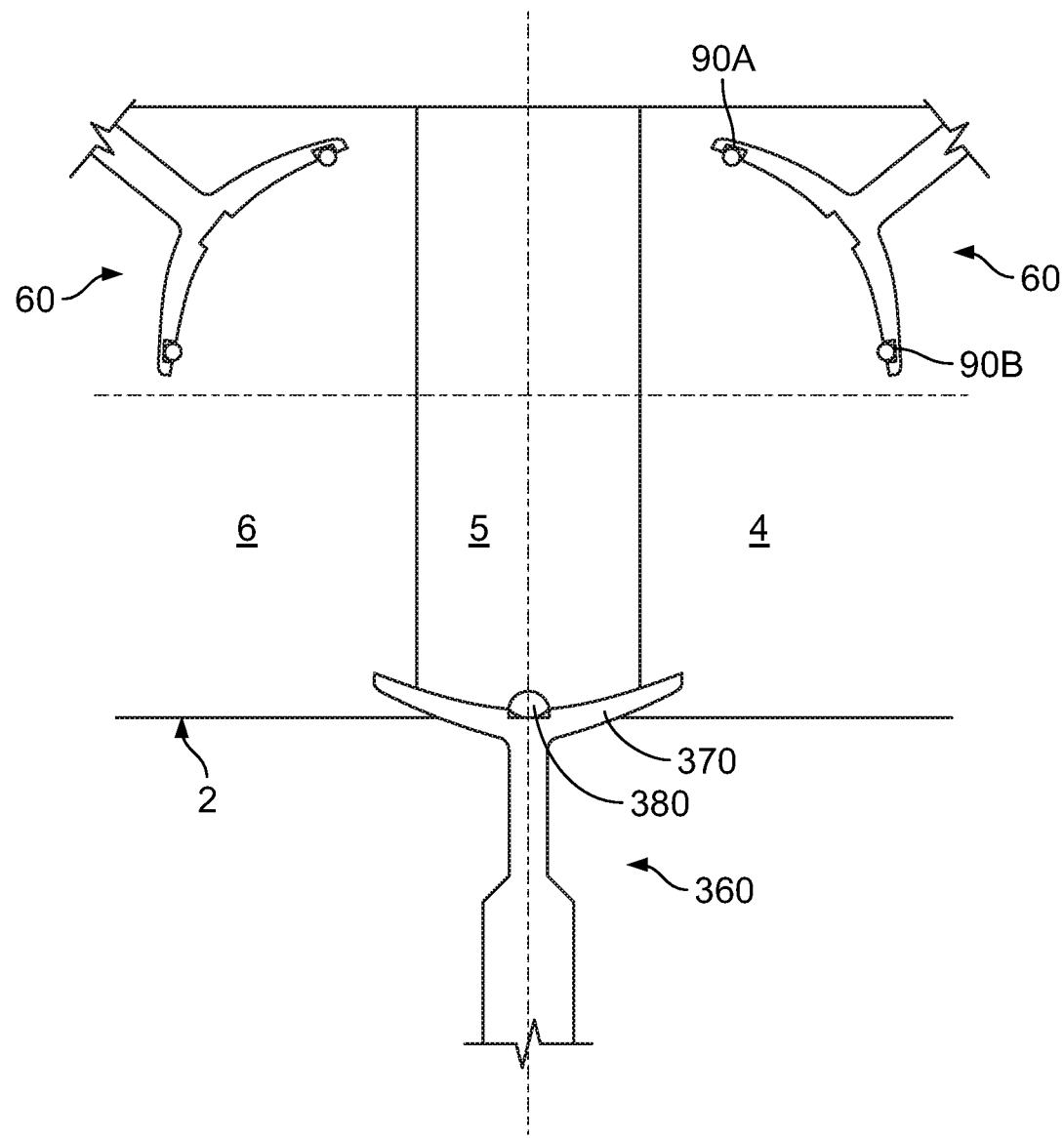
FIG. 23 is a top view of a surgical access portal created through a surgical technique performed according to one embodiment of the disclosure.

In yet another embodiment, a surgical technique involves the same steps as described above up to and including advancement and positioning of composite blade 360, although once composite blade 360 is in position over a vertebral body within the patient, two double pin blades 60 are used to complete the requisite retraction to create the surgical access portal, instead of the retraction instrument. Here, each double pin blade 60 is inserted into the surgical access portal using an antero-lateral approach so that respective blades 60 are positioned over a vertebral body, as shown in FIG. 23. The positioning of each blade 60 is performed so that the three blades are approximately equidistant from one another, again, shown in FIG. 23. However, the position of each tool in the body may vary depending on the surgery. In some examples, curved tip 64 of blade 60 is used to guide the blade over a curved vertebral surface 4, 6 and provide increased surface contact between the blade and the vertebral surface.

Once double pin blades 60 are in position, they may be manually held in place for the surgical procedure or they may be externally fixed using a rigid arm (not shown). Optionally, one or two bone pins 90A, 90B may be disposed within grooves on blade 60 and advanced into a vertebral body below the blade 60 to provide additional support for the surgical access portal. This may be done for one or both blades. In the embodiment shown in FIG. 23, the bone pins 90A, 90B are longer than the blade so the bone pins may be actuated from above the blade while also penetrating a vertebral body below the blade. When the pin(s) is secured to the vertebral body, the blade(s) is rigidly attached to the vertebral body for the remainder of the surgical procedure. This approach is advantageous as it provides the option for additional rigidity in the blade in addition to the rigidity provided by a rigid arm. Further, the option of securing a single blade to a bone with two pins provides rotational stability along with axial stability.

Additionally, in other examples of the surgical technique, a light emitting structure, such as a fiber optic light bar (not shown), may be clipped onto upper and lower central recess 76A, 77 of double pin blade 60 and slid down to a desired location on the blade to direct light into the surgical access portal. The blade may further include a preset stop with a highly reflective surface. In this manner, once a distal end of the light bar is positioned at the preset stop, light may be directed into a working area of the surgical portal. Similarly, a light bar or light pipe may be inserted through a cannulation in the rod and advanced to a preset stop at an end of the cannulation on a side of the rod, the preset stop directing light into the portal. The light emitting structure may also be clipped to blade 260 in the same manner. Other lighting technologies contemplated for inclusion on the rods of the retraction instrument and the blades of the present disclosure include those described in WO2019/036048, the disclosure of which is hereby incorporated by reference herein in its entirety.

In yet another embodiment, the surgical method employs composite blade 760, shown in FIGS. 24 and 25, in place of composite blade 360. In this method, outer blade component 770 is initially advanced into the patient. Blade 770 may be advanced with or without a light transmitting structure 785 disposed therein. In some examples, the light emitting structure may be slid onto blade 770 after the blade is in position. Once blade 770 is in position over vertebrae 2, inner blade structure 780 is advanced at a desired angle, such as that shown in FIG. 25, or at a varying angle, toward a target site in the patient. When curved distal portion 783 is near distal end 773 of outer blade component 770, it is carefully advanced over the distal end and rotated outward away from blade 770 to push anatomy on the concave side of curved distal portion 783 backward to improve access around the target site. Adjustments to a position of blade component 780 may be made as desired and once a final position is decided upon, inner blade component 780 is secured in position using a separate securement mechanism from that used to secure outer blade component 770.

The surgical method may be varied in many ways. Various combinations of the blades disclosed herein, including blades 60, 160, 260, 360, 460, 560, 660 and 760 may be used to create a surgical access portal to access the spine. Any number of these blades may be used in combination with any retraction instrument 10, 110, 210. When blades 160, 260, 460, 560, 660, 760 are used to create a surgical portal, the curved distal end of the applicable blade may also mate with an intervertebral disc or vertebral body to obtain increased surface area contact between the blade and the vertebral surface. Additionally, the rods for each of the retraction instruments may be removed and used interchangeably with lateral trans-psoas retractor systems, such as those described in the '228 Publication.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A kit for creating access to a surgical site comprising:
   an instrument including two rods attached to a main body of the instrument, the rods having a convex surface around a perimeter of the rods and along a length of the rods;
   a pin holder engageable over the convex surface of one of the rods, the pin holder including a bone pin disposed therein; and
   a blade separate from the instrument and having a length including a linear portion and a curved portion, the curved portion defining an engagement end of the blade and curving out of a plane through opposing lateral edges of the linear portion, each of the linear and curved portions having a concave surface, the concave surface spanning continuously along the linear and curved portions,
   wherein when the instrument and the blade are inserted into a patient, the blade is oriented such that the concave surface of the blade faces the instrument to create a surgical access portal.

2. The kit of claim 1, wherein when the pin holder is engaged to one of the rods, the bone pin of the pin holder is parallel to the rod to which the pin holder is engaged.

3. The kit of claim 1, wherein each rod of the instrument is approximately perpendicular to the main body and has a cylindrical shape over part of its length.

4. The kit of claim 1, wherein the blade includes a distal portion curved in a direction such that the blade is entirely on one side of a plane through lateral edges of the concave surface of the linear portion.

5. The kit of claim 4, wherein the distal portion of the blade is tapered.

* * * * *